(12) United States Patent
Magnelli et al.

(10) Patent No.: US 9,964,548 B2
(45) Date of Patent: *May 8, 2018

(54) DEGLYCOSYLATION REAGENTS AND METHODS

(71) Applicant: New England Biolabs, Inc., Ipswich, MA (US)

(72) Inventors: Paula Magnelli, Somerville, MA (US); Ellen Guthrie, Andover, MA (US); Christopher H. Taron, Essex, MA (US); Ming-Qun Xu, Hamilton, MA (US); John Buswell, Byfield, MA (US)

(73) Assignee: New England Biolabs, Inc., Ipswich, MA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/392,908

(22) Filed: Dec. 28, 2016

(65) Prior Publication Data

US 2017/0138959 A1 May 18, 2017

Related U.S. Application Data

(63) Continuation of application No. 14/725,614, filed on May 29, 2015.

(Continued)

(51) Int. Cl.
*G01N 33/68* (2006.01)
*C07K 1/12* (2006.01)
(Continued)

(52) U.S. Cl.
CPC ........... *G01N 33/6854* (2013.01); *C07K 1/12* (2013.01); *C07K 14/525* (2013.01); *C07K 16/00* (2013.01);
(Continued)

(58) Field of Classification Search
None
See application file for complete search history.

(56) References Cited

U.S. PATENT DOCUMENTS

2010/0304436 A1* 12/2010 Chen ...................... C07K 16/00
435/69.6
2013/0186797 A1* 7/2013 Walsh ................ A61K 39/3955
206/459.5

FOREIGN PATENT DOCUMENTS

AU          749719        3/2000
WO    WO 2009/155324 A2   12/2009
WO    WO 2013/084236 A1    6/2013

OTHER PUBLICATIONS

Sigma, "Enzymatic Deglycosylation" (print retrieved Apr. 13, 2017).*

(Continued)

*Primary Examiner* — Tracy Vivlemore
*Assistant Examiner* — Nam P Nguyen
(74) *Attorney, Agent, or Firm* — New England Biolabs, Inc; Harriet M. Strimpel

(57) ABSTRACT

Compositions and methods are provided for efficiently preparing a completely deglycosylated antibody where efficiency is measured in relative amounts of reagents in soluble or lyophilized form, and time and temperature of the reaction. Compositions and methods are also provided for separating substantially all N-linked glycans from a glycosylated antibody and for preserving functionality of the antibody. The methods are compatible with glycan labeling and protease digestion without the need for prior purification steps.

26 Claims, 18 Drawing Sheets

Related U.S. Application Data

(60) Provisional application No. 62/080,480, filed on Nov. 17, 2014, provisional application No. 62/040,745, filed on Aug. 22, 2014, provisional application No. 62/021,936, filed on Jul. 8, 2014, provisional application No. 62/018,074, filed on Jun. 27, 2014, provisional application No. 62/005,559, filed on May 30, 2014.

(51) Int. Cl.

| | |
|---|---|
| *C07K 16/00* | (2006.01) |
| *C07K 16/28* | (2006.01) |
| *C07K 16/24* | (2006.01) |
| *C07K 14/525* | (2006.01) |
| *C12N 9/80* | (2006.01) |
| *C12N 9/76* | (2006.01) |
| *C12N 9/10* | (2006.01) |
| *G01N 33/535* | (2006.01) |
| *G01N 33/543* | (2006.01) |
| *C12N 9/96* | (2006.01) |

(52) U.S. Cl.
CPC ........ *C07K 16/241* (2013.01); *C07K 16/2863* (2013.01); *C07K 16/2887* (2013.01); *C12N 9/1007* (2013.01); *C12N 9/6427* (2013.01); *C12N 9/80* (2013.01); *C12N 9/96* (2013.01); *C12Y 201/01063* (2013.01); *C12Y 304/21004* (2013.01); *C12Y 305/01052* (2013.01); *G01N 33/535* (2013.01); *G01N 33/543* (2013.01); *C07K 2317/40* (2013.01); *C07K 2319/30* (2013.01)

(56) References Cited

OTHER PUBLICATIONS

Parent et al., "ANKRD13C Acts as a Molecular Chaperone for G Protein-coupled Receptors", Journal of Biological Chemistry, vol. 285, No. 52, pp. 40838-40851, published Dec. 24, 2010.*
New England Biolabs, Enzymatic removal of N- and O-glycans using PNGase F or the Protein Deglycosylation Mix, Glycobiology & Protein Tools, published Oct. 2011.*
Yu et al., "A rapid sample preparation method for mass spectrometric characterization of N-linked glycans", Rapid Commun. Mass Spectrom, vol. 19, pp. 2331-2336, published 2005.*
Masuda et al., "Unbiased Qunatitation of *Escherichia coli* Membrane Proteome Using Phase Transfer Surfractants", Molecular & Cellular Proteomics, vol. 8.12, pp. 2770-2777, published 2009.*
Kwan et al., "N-Glycosidase-carbonhydrate-binding module fusion proteins as immobilized enzymes for protein deglycosylation", Protein Engineering, Design & Selection, vol. 18, No. 10, pp. 497-501, published 2005.*
Uhenheuer et al., "Direct Supramolecular Surface Assembly of SNAP-tag Fusion Proteins", Chem. Eur. J., vol. 18, pp. 6788-6794, published 2012.*
SNAP-tag Technologies: Novel Tools to Study Protein Function, print retrieved online <https://www.neb.com/tools-and-resources/feature-articles/snap-tag-technologies-novel-tools-to-study-protein-function>, Aug. 29, 2017.*
Qualtiere et al., "Effects of Ionic and nonionic detergents on antigen-antibody reactions", The Journal of Immunology, vol. 119, No. 5, published Nov. 1977.*
Bardor, et al., "Analytical strategies to investigate plant N-glycan profiles inthe context of plant-made pharmaceuticals", Current Opinion in Structural Biology, 2006, 16:576-583.
Biofiles, "Detergents and Solubilization Reagents", G-Biosciences "Detergents: A handbook and Selection Guide to Detergents and Detergent Removal", 2008, vol. 3 No. 3.
Brown, et al., "Purification and characterization of glycolipid transfer protein from bovine brain", Biochimica et Biophysica Acta, 1990, 1044(1):77-83.
Cole, et al., "The Jpred 3 secondary structure prediction server", Nucleic Acids Research, 2008, 36, W197-W201.
Falk, et al., "Enhancing effects of bile salts on the degradation of glycosphingolipids by glycosidases from bacteria of the human fecal flora", Biochimica et Biophysica Acta—Lipids and Lipid Metabolism, 1991, 1084(2):139-148.
Hofmann, et al., "Bile salts of vertebrates: structural variation and possible evolutionary significance", Journal of Lipid Research, 2010, 51:226-246.
Holm et al., "Incorporation of Hormone-Sensitive Lipase into Phosphatidylcholine Vesicles", LIPIDS, 1990, 25(5): 254-259.
Jenkins, et al., "Post-translational Modifications of Recombinant Proteins: Significance for Biopharmaceuticals", Mol Biotechnol, 2008, 39(2):113-118.
Liu, et al., "Heterogeneity of Monoclonal Antibodies", Journal of Pharmaceutical Sciences, 2008, 97(7): 2426-2447.
Magnelli, et al., "Identification and Characterization of Protein Glycosylation using Specific Endo- and Exoglycosidases", Journal of Visualized Experiments, 2011, No. 58.
McCormick, et al., "Plant-produced idiotype vaccines for the treatment of non-Hodgkin's lymphoma: Safety and immunogenicity in a phase I clinical study", PNAS, 2008, 105(29): 10131-10136.
Russel, "The Enzymes, Regulation, and Genetics of Bile Acid Synthesis", Annu. Rev. Biochem., 2003, 72:137-174.
Savelli, et al., "Enzyme activity and stability control by amphiphilic self-organizing systems in aqueous solutions", Current Opinion in Colloid & Interface Science, 2000, 5:111-117.
"Program and Abstract for the 2013 Annual Conference of the Society for Glycobiology", Annual Conference of the Society for Glycobiology, 2013, pp. 1307-1412.
Rawlings, Membrane proteins: always an insoluble problem? Biochem Soc Trans. (2016) 44: 790-795.
Moraes, et al., Membrane protein structure determination—The next generation. Biochimica et Biophysica Acta (2014) 1838: 78-87.

* cited by examiner

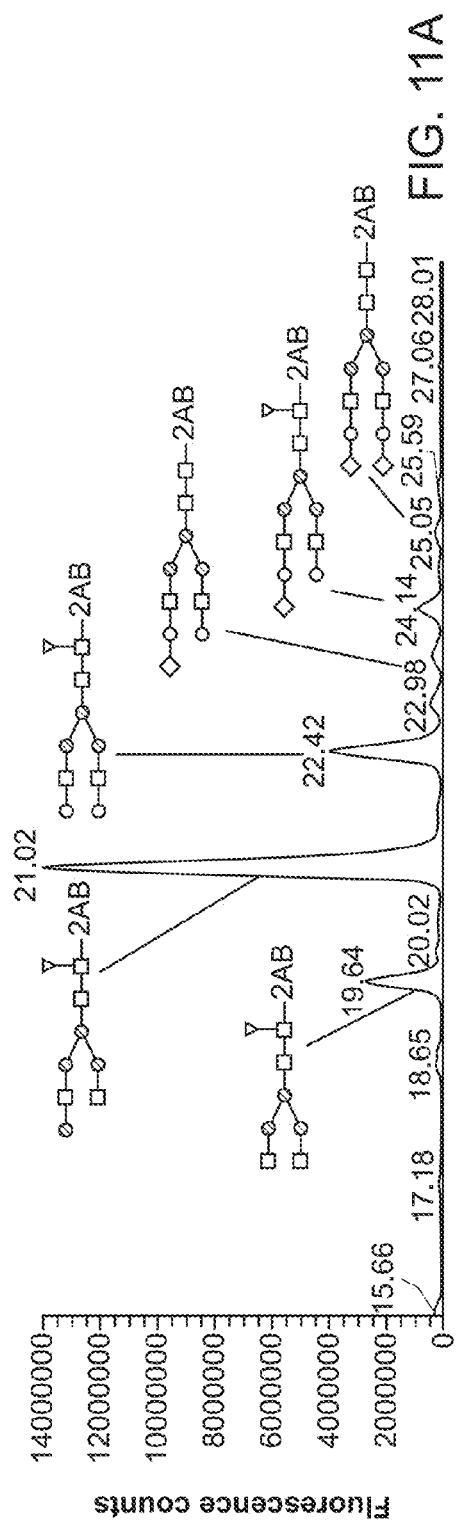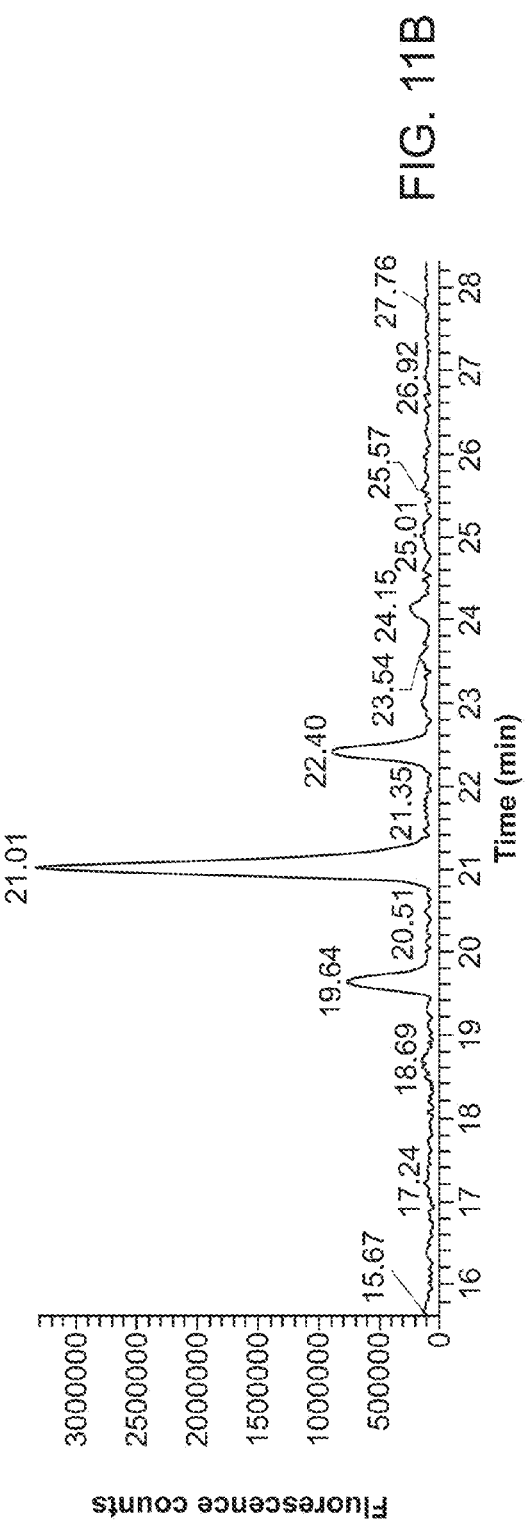
FIG. 11A
FIG. 11B

SEQUENCE LISTING

```
<160> NUMBER OF SEQ ID NOS: 1

<210> SEQ ID NO 1
<211> LENGTH: 586
<212> TYPE: PRT
<213> ORGANISM: Artificial Sequence
<220> FEATURE:
<223> OTHER INFORMATION: Synthetic construct

<400> SEQUENCE: 1

Ala Ala Val Pro His Arg His Arg Leu Pro Ser His His Leu Ala Ser
1               5                   10                  15

Leu Lys Leu Asn Ala Ser Ala Pro Pro Thr Thr Tyr Phe Glu Val Asp
            20                  25                  30

Arg Pro Ile Arg Pro Pro Arg Gly Ser Val Gly Pro Cys Ser Thr Leu
        35                  40                  45

Leu Leu Ser Asn Ser Phe Gly Ala Thr Tyr Gly Arg Pro Pro Val Thr
    50                  55                  60

Ala Ala Tyr Ala Pro Pro Ser Cys Leu Ala Gly Gly Gly Gly Gly Gly
65                  70                  75                  80

Gly Gly Ala Ser Ser Ile Ala Leu Ala Val Leu Glu Trp Ser Ala Asp
                85                  90                  95

Cys Arg Gly Arg Gln Phe Asp Arg Ile Phe Gly Val Trp Leu Ser Gly
            100                 105                 110

Ala Glu Leu Leu Arg Ser Cys Thr Ala Glu Pro Arg Ala Thr Gly Ile
        115                 120                 125

Val Trp Ser Val Ser Arg Asp Val Thr Arg Tyr Ala Ala Leu Leu Ala
    130                 135                 140

Glu Pro Gly Glu Ile Ala Val Tyr Leu Gly Asn Leu Val Asp Ser Thr
145                 150                 155                 160

Tyr Thr Gly Val Tyr His Ala Asn Leu Thr Leu His Leu Tyr Phe His
                165                 170                 175

Pro Ala Pro Pro Pro Pro Pro Gln Gln Ala Asp Leu Ile Val
            180                 185                 190

Pro Ile Ser Arg Ser Leu Pro Leu Asn Asp Gly Gln Trp Phe Ala Ile
        195                 200                 205

Gln Asn Ser Thr Asp Val Gln Gly Lys Arg Leu Ala Ile Pro Ser Asn
```

```
            210                 215                 220
Thr Tyr Arg Ala Ile Leu Glu Val Phe Val Ser Phe His Ser Asn Asp
225                 230                 235                 240

Glu Phe Trp Tyr Thr Asn Pro Pro Asn Glu Tyr Ile Glu Ala Asn Asn
                245                 250                 255

Leu Ser Asn Val Pro Gly Asn Gly Ala Phe Arg Glu Val Val Val Lys
                    260                 265                 270

Val Asn Asp Asp Ile Val Gly Ala Ile Trp Pro Phe Thr Val Ile Tyr
                275                 280                 285

Thr Gly Gly Val Asn Pro Leu Leu Trp Arg Pro Ile Thr Gly Ile Gly
    290                 295                 300

Ser Phe Asn Leu Pro Thr Tyr Asp Ile Asp Ile Thr Pro Phe Leu Gly
305                 310                 315                 320

Lys Leu Leu Asp Gly Lys Glu His Asp Phe Gly Phe Gly Val Thr Asn
                    325                 330                 335

Ala Leu Asp Val Trp Tyr Ile Asp Ala Asn Leu His Trp Leu Asp His
                340                 345                 350

Lys Ser Glu Glu Thr Thr Gly Ser Leu Ile Ser Tyr Glu Ala Gln Gly
                355                 360                 365

Leu Val Leu Asn Val Asp Ser Gly Phe Ser Gly Leu Asp Gly Gln Phe
        370                 375                 380

Val Thr Ser Ala Ser Arg His Ile Ser Ala Thr Gly Leu Val Lys Ser
385                 390                 395                 400

Ser Tyr Gly Glu Val Thr Thr Asn Phe Tyr Gln Arg Phe Ser Tyr Val
                    405                 410                 415

Asn Ser Asn Val Tyr Ser Lys Asn Gly Ser Val Gln Val Val Asn Gln
                420                 425                 430

Thr Ile Asp Ala Lys Ser Gly Val Phe Ala Lys Asp Ala Leu Ala Val
                435                 440                 445

Leu Leu Ser Glu Glu Leu His Gln Ile Phe Pro Leu Tyr Val Tyr Thr
450                 455                 460

Gly Thr Ser Asp Glu Glu Ala Asp Glu Tyr Thr Leu Ile Ser His Val
465                 470                 475                 480

Lys Leu Gly Val Asn Glu Lys Glu Thr Ser Gly Lys Met Gly Phe
                    485                 490                 495

Ser Tyr Asn Ser Leu Arg Asn Ala Gln Ser Ala His Gly Ser Met Lys
                500                 505                 510

Val Lys Lys Asn Leu Val Val Gly Gly Leu Gly Glu Thr His Gln Ala
                515                 520                 525

Tyr Lys Tyr Val Gly Ala Asp Gly Cys Tyr Phe Arg Asp Val Arg Ser
                530                 535                 540

Lys Asn Tyr Thr Val Leu Ser Asp His Ser Gly Asp Ser Cys Thr Lys
545                 550                 555                 560

Arg Asn Pro Tyr Asn Gly Ala Lys Phe Ser Leu Arg Asn Asp Gln Ser
                565                 570                 575

Ala Arg Arg Lys Leu Met Val Asn Asn Leu
                580                 585
```

DEGLYCOSYLATION REAGENTS AND METHODS

CROSS REFERENCE

This application is a Continuation of U.S. patent application Ser. No. 14/725,614, filed May 29, 2015, which claims right of priority to U.S. Provisional Application Ser. No. 62/005,559, filed May 30, 2014, 62/018,074, filed Jun. 27, 2014, 62/021,936 filed Jul. 8, 2014, 62/040,745 filed Aug. 22, 2014 and 62/080,480 filed Nov. 17, 2014.

BACKGROUND

It is estimated that over 50% of human proteins are glycosylated. Many health and disease biomarkers are glycosylated proteins and specific glycoforms may be correlated with health or disease state. This includes glycosylated proteins linked to cancer, diabetes, inflammation and other medical conditions, as well as development. Furthermore, glycosylated proteins are not just limited to human or mammals, but are found in all eukaryotic systems, as well as prokaryotes, Archaea and plants.

Antibodies are glycoproteins. The glycans on an antibody can be structurally heterogeneous and can vary significantly in health and disease. During antibody production in vitro, the glycans attached to an antibody are affected not only by the cell type used for its production, but also by the cell culture conditions. Changes in nutrient availability, pH, cell density and $CO_2$ levels can markedly alter the antibody glycoforms produced by the cells. For therapeutic antibodies, this can affect tissue distribution, serum half-life, resistance to proteolysis, complement activation, antibody-dependent cytotoxicity (ADCC), and inflammation. Consequently, it is desirable to manufacture therapeutic antibodies within specific regulatory-approved limits for glycoform variation.

Glycan profiling of glycoproteins such as antibodies requires methods for testing and identifying glycoforms in an antibody sample. Analysis of glycan structure is an unstandardized, time-consuming and low-throughput process with deglycosylation incubation times of as much as 16 hours under conditions that not only result in partial deglycosylation but also risk damage to the proteins. (Jenkins, et al., *Mol Biotechnol.* 39(2):113-8 (2008); Liu, et al., *J Pharm Sci.* 97(7):2426-47 (2008). Attempts to shorten the incubation period have resulted in the use of detergents that affect the protein integrity and hence functionality and interfere with mass spectrometry. Antibodies can be difficult to deglycosylate because glycans can be buried within the molecule's structural fold. Standard methods denature the antibody structure to expose the glycans using such methods as extreme heat and harsh denaturants like sodium dodecyl sulfate (SDS). However, these methods have several drawbacks: for example SDS can denature the enzymes used to remove glycans, SDS is difficult to remove, and even trace amounts of SDS can interfere with sample analysis methods like mass spectrometry. These methods are also time-consuming. Alternative methods attempt to increase the rate of deglycosylation by using a high concentration of Peptide-N-Glycosidase F (PNGase F). However, this approach does not overcome the presumed and undesirable bias associated with partial deglycosylation. Partial deglycosylation may result in certain glycoforms being preferentially released from the protein over others. This approach is also costly and is not readily scalable as it requires significant amounts of PNGase F.

Current approaches to improve deglycosylation for antibody characterization continue to result in ever more complex methods, require additional time to process, are inefficient, and incompletely remove glycans. Furthermore, the production of deglycosylated antibodies is currently limited to site-mutagenesis or bacterial expression systems. Unfortunately, these systems have difficulties in producing properly assembled and folded antibodies in any meaningful quantity.

SUMMARY

In general, preparations including compositions and methods of use are described for completely deglycosylating proteins such as antibodies resulting in unbiased removal of glycans that are the substrates of the glycosidase or mixture of glycosidases used in the deglycosylation reaction. Also described are methods and reagents for separating glycans from the protein for further analysis of the glycans which may be optionally labeled. Where this involves peptide cleavage by means of a protease, surprisingly it has been shown that peptide cleavage and deglycosylation can be achieved in a single step. For ease of use the glycosidase and/or buffer compositions may be lyophilized and added to the glycosylated protein to effect deglycosylation.

In general in one aspect, an artificial in vitro preparation or composition that cannot occur in nature is provided that includes (i) a bile salt or a detergent not including sodium dodecyl sulfate (SDS); (ii) one or more glycosidases; (iii) a completely deglycosylated antibody as determined by electrophoresis or by mass spectrometry; and (iv) glycan cleavage products. In one aspect, the detergent is a dialyzable non-cleavable carboxylate anionic surfactant. In general, in another aspect, an artificial in vitro preparation or composition that cannot occur in nature is provided that includes (a) a bile salt or a dialyzable non-cleavable carboxylate anionic surfactant; (b) one or more glycosidases; (c) a completely deglycosylated biologically active protein as determined by electrophoresis or by mass spectrometry; and (d) glycan cleavage products.

In another aspect, the completely deglycosylated antibody has antigen binding activity and may be used in immunoassays. In another aspect, the glycan cleavage products and/or the antibody are labeled with a fluorescent label, a radioisotope, methyl acetyl, an antibody or a combination thereof. This may facilitate analysis of the glycan type as well as determining glycan binding sites on the protein. Examples of a deglycosylated protein include antibodies. Examples of representative antibodies include deglycosylated human IgG1, human IgG2, human IgG3, human IgG4, human IgM, human IgA1, human IgA2, human IgE, murine IgG1, murine IgG2a and murine IgA.

In another aspect, a protease may be included in the composition, wherein the protease may be, for example, trypsin. Other examples of proteases may include GluC, AspN, proteinase K, Factor Xa, Enterokinase, LysC, Arg-C, LysN, IdeS, V-8 Protease, Papain, Alpha-Lytic Protease, Pyroglutamate Aminopeptidas, Leucine Aminopeptidase, Methionine Aminopeptidase, Aminopeptidase I, Aminopeptidase A, Carboxypeptidases (A, B, G, Y), pepsin, Cathepsins (B, C, D), α-Chymotrypsin, TEV, thrombin, IdeZ and IdeE.

In another aspect, the glycosidase (one or more glycosidases) may be a plurality of glycosidase and may include for example, one or more exoglycosidases and/or one or more endoglycosidases. One or more of the glycosidases may be a fusion protein where for example, the fusion protein may be immobilized on a matrix. An example of a fusion protein includes a mutant O6-alkylguanine-DNA-alkyltransferase (AGT) which can optionally be immobilized through affinity binding of the AGT to a matrix. The glycosidase or one or more glycosidases may include one or more N-glycan glycosidases, one or more O-glycosidases and/or one or more endoglycosidases.

In another aspect, the composition may include an aqueous buffer.

In general in one aspect, a method is provided that includes (a) incubating a composition comprising a dialyzable non-cleavable carboxylate surfactant, not including sodium dodecyl sulfate (SDS), and/or a bile salt; and one or more glycosidases with a glycosylated antibody for less than 60 minutes; and (b) completely cleaving glycans from the glycosylated antibody to form a deglycosylated antibody and glycan cleavage products.

In one aspect of the method the deglycosylated antibody and/or cleaved glycan products are isolated and optionally purified. The antigen binding activity of the deglycosylated antibody may be characterized. The antigen binding properties of the antibody when tested were found to be preserved. Binding of deglycosylated antibody to antigen could be quantified using antibody-antigen binding assay selected from, for example, a radioimmune assay, an ELISA, an affinity binding assay, or an immunoprecipitation assay. The deglycosylated antibodies are suitable for therapeutic and/or diagnostic use.

In one aspect of the method, a protease such as trypsin is contained within the composition containing one or more glycosidases for cleaving protein into deglycosylated peptide fragments and glycan cleavage products.

In one aspect, the composition is lyophilized prior to incubating with glycosylated antibody wherein the glycosylated antibody is in an aqueous buffer. In another aspect, the glycosidase is immobilized on a matrix. In one aspect, the incubating is at a temperature of about 20° C.-60° C. In another aspect, incubating is for a time of 5 minutes or less.

In general in one aspect, a kit is described containing one or more lyophilized glycosidases, and/or one or more immobilized glycosidases, or one or more glycosidases in solution and a lyophilized buffer or non-lyophilized buffer, or a combination thereof, wherein the lyophilized or non-lyophilized buffer comprises: a bile acid; or a dialyzable non-cleavable carboxylate anionic surfactant, excluding SDS; or a combination thereof.

BRIEF DESCRIPTION OF THE DRAWINGS

The figures and drawings are intended to illustrate one or more versions of the compositions and/or methods described herein. Unless stated otherwise, these are not intended to be limiting for the purpose of interpreting the scope of any claims.

FIG. 1A shows a diagram of an antibody composed of two heavy chains (H, white); two light chains (L, grey) and glycan molecules (G) attached to the heavy chain. Preferably, there are no glycans in a completely deglycosylated antibody molecule.

FIG. 1B is a control ("no pre-treatment" and "no PNGase F" treatment) showing the profile of glycoforms present in the starting monoclonal IgG antibody sample. The cartoons illustrate the glycoform for each observed major peak.

FIG. 1C shows the profile of antibody pre-treated by heat and incubated with PNGase F for 1 hour. The four major peaks (mass 50191, 50353, 50516, and 50823) represent fully glycosylated glycoproteins. Under these conditions, less than approximately 10% of the antibody heavy chain is deglycosylated (see cartoon of an antibody heavy chain without an attached glycan at far left peak, near mass 48747).

FIG. 1D shows that heat combined with an extended 16 hour PNGase F incubation does not result in a substantially deglycosylated antibody. Increasing the PNGase F incubation time to 16 hours increased the amount of deglycosylated heavy chain fraction slightly, but a substantial proportion of the antibody is still glycosylated as evidenced by the major glycosylated glycoprotein peaks at 50191, 50353, 50516, and 50823.

FIG. 2A is the control showing the profile of glycoproteins present in the starting monoclonal IgG antibody sample (no pre-treatment and no PNGase F treatment).

FIG. 2B is the profile of antibody pre-treated by heat denaturation in combination with a reducing agent dithiothreitol (DTT) and incubated with PNGase F for 1 hour. The combination pre-treatment did not improve deglycosylation as compared to heat denaturation alone (compare FIG. 1B and FIG. 2B). The antibody heavy chain remains substantially glycosylated, with less than 10% deglycosylated (see peak near mass size 48750).

FIG. 2C shows that the same pre-treatment with an extended 16 hour PNGase F incubation also failed to substantially deglycosylate the antibody heavy chain. Only partial deglycosylation was achieved as evidenced by the three remaining major peaks for the shown glycoforms. Bias in the deglycosylation rate of certain glycoforms is evidenced by the absence of the fourth glycoform (indicated by the arrow). This demonstrates that that different glycoforms are deglycosylated at different rates under these reaction conditions.

FIG. 3A is a control (no PNGase F) showing the antibody heavy chain glycoforms present in the original sample (mass 50192, 50354, and 50823).

FIG. 3B demonstrates that substantially all heavy chain glycoforms (indicated by the arrow) were still present after using RapiGest. Only a small fraction of antibody heavy chain was deglycosylated (mass 48748).

FIG. 4A compares reaction conditions using 0.2 mM, 1 mM, 4 mM and 20 mM DTT in combination with 0%, 0.05%, 0.1%, 0.5% LS.

FIG. 4B compares reaction conditions using 20 mM, 40 mM and 80 mM DTT in combination with 0%, 0.2%, 0.4%, 0.5% LS.

FIG. 4C compares reaction conditions using 4 mM and 20 mM DTT in combination with 0%, 0.5%, 2%, 4% and 5% LS.

FIG. 7A: A one-step reaction of 5 minutes incubation with PNGaseF performed over different temperatures. The results with two different buffers are shown.

FIG. 7B: A two-step reaction with a pretreatment incubation of 5 minutes at 50° C. and a subsequent 5 minute incubation with PNGase F performed over different temperatures. The results with two different buffers are shown.

FIG. 10A shows the glycans (A to I) released from the glycosylated antibody when incubated with PNGase F and a reducing agent (DTT) in the presence of the bile salt, SDC (hatched bars); or PNGase F and DTT only (white). A minimum ten-fold increase in glycan yield was observed when DTT plus SDC was used compared with DTT only in peak fractions. The ten-fold increase is indicative of the efficient and substantially complete removal of all glycans from the antibody by this method.

FIG. 10B provides pie charts showing the percentage composition of IgG N-glycans after deglycosylation using:
 (i) DTT and SDC; the precise composition of the N-glycans present in the monoclonal IgG sample is provided showing an unbiased representation of substantially all nine types of glycans.
 (ii) DTT only: in contrast to (i), not all glycans are removed where the major N-glycans (D and B) are underrepresented and minor glycans species (A, H, E and I) are overrepresented compared to deglycosylation in the presence of DTT and SDC and hence showing a bias in the removal of N-glycans by PNGase F in the presence of a reducing agent alone.

FIGS. 11A-11B show the chromatographic profiles of fluorescently labeled N-glycans released from an antibody and labeled in a one pot method FIG. 11A or a two pot method FIG. 11B (see also Example 11). The glycans were cleaved from a monoclonal IgG antibody using PNGase F in the presence of DTT and SDC. The glycans cleaved from the antibody were either labeled directly in the deglycosylation mixture in a one pot method, or first isolated from the deglycosylation mixture before labeling in a two pot method. Whereas the overall profile in FIGS. 11A and 11B were similar, the absolute quantities of glycans were significantly increased in the one pot method (compare fluorescent counts on y-axes of FIGS. 11A and 11B) indicating the efficiency of the one pot method.

FIG. 11A shows the overall profile of labeled glycans using a one pot method where the glycans were not isolated prior to labeling.

FIG. 11B shows the overall profile of labeled glycans using a two pot method where the glycans were first isolated prior to labeling.

FIG. 12A is the N-glycan profile of rituximab.

FIG. 12B is the N-glycan profile of cetuximab.

FIG. 12C is the N-glycan profile of etanercept.

FIG. 13A is an SDS-PAGE of each treated sample. The deglycosylated heavy chain of IgG runs slightly faster (lower) than the glycosylated heavy chain (as indicated by arrows with cartoons of the glycosylated and deglycosylated heavy chain). (+) is an anti-MBP antibody treated with PNGase F in the presence of SDC and a reducing agent; (−) is a parallel sample but with no PNGase F treatment.

FIG. 13B is ESI-TOF MS analysis for the sample treated with PNGase F in the presence of a surfactant and a reducing agent shows substantial deglycosylation of the antibody. The negative control shows the antibody glycoforms present in the original sample when not treated with PNGase F.

FIG. 13C confirms that the deglycosylated antibody of the positive sample is functional and retains its ability to recognize and bind to its antigen similar to the glycosylated antibody. A western blot was performed on an MBP-fusion protein. The white triangles above the gel indicate the decreasing amounts of the cognate antigen from 4.2 ng to 0.5 ng loaded on the gel that was blotted.

FIG. 14A shows the SDS-PAGE of a monoclonal IgG completely deglycosylated with lyophilized PNGase F and buffer (dried together or separately). The arrows indicate that the shift in migration corresponds to full deglycosylation of the IgG, comparable with the positive control ("fresh PNGase F"), which used PNGase F and buffer that had not been lyophilized (shown on right). PNGase F was absent from the negative controls ("C").

FIG. 14B is the ESI-TOF MS analysis for the samples described in FIG. 14A ((i) complete deglycosylation using a lyophilized master mix (PNGase F-buffer); (ii) complete deglycosylation using lyophilized PNGase F lyophilized buffer); (iii) negative control (no PNGase F)). The analysis confirms that the lyophilized and rehydrated buffer and enzyme substantially deglycosylates the antibody in 5 minutes at 50° C.

FIG. 15A Antibody isotypes: hIgG1, hIgG2, and hIgG4.

FIG. 15B Antibody isotypes: hIgM, hIgA1, hIgE, mIgG1, mIgG2A.

FIG. 16A shows complete deglycosylation of a monoclonal IgG using 62.5 Units of PNGase F and where the reaction buffer contains 0.5% LS (see black arrow).

FIG. 16B shows that, when LS is absent, even the most concentrated stock available (4000 units) is not sufficient for complete deglycosylation (indicated by an X).

FIG. 17A shows complete deglycosylation of a monoclonal IgG using 62.5 Units of PNGase F and where the reaction buffer contains 0.5% (see black arrow).

FIG. 17B shows that, when LS is absent, even the most concentrated stock available (4000 units) is not sufficient for complete deglycosylation (indicated by an X).

FIG. 18A shows that rapid deglycosylation of antibodies is effective in the absence of a reducing agent with pretreatment for 2 to 15 minutes at temperatures ranging from 80° C. to 55° C. The SDS-PAGE shows a shift in size (indicated by the arrows), corresponding to complete deglycosylation.

FIG. 18B shows that rapid deglycosylation will preserve the structure of the antibody in the absence of a reducing agent. To detect the presence of multimeric proteins (i.e. IgG hetero-tetramers) the samples were also run on SDS PAGE without DTT in the sample buffer. It is evident that the multimeric structure has been preserved, notice the lack of monomeric structures running under the 80KD marker.

FIG. 18C shows the functional activity for a deglycosylated, intact, monoclonal anti-MBP, by it recognition of the corresponding antigen (MBP-tagged protein) with equivalent potency compared with the pre-incubated antibody, or with fresh antibody (both of which are still glycosylated).

FIG. 20A shows the total ions observed from the PNGase F/Trypsin digestion. The reaction performed on Tris HCl buffer (optimal for Trypsin activity) showed the same peptide coverage in the absence of LS as predicted in the presence of LS.

FIG. 20B shows the fragmentation pattern of the isolated EDYnSTIR peptide, which corresponds to the unique glycosylation site of mouse IgG. The peptide is only found as the aspartic acid form, indicating that deglycosylation was complete.

DETAILED DESCRIPTION

Figure 1A:
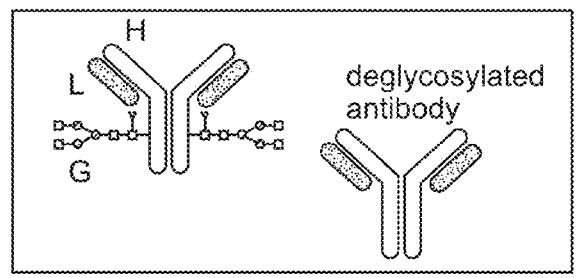
FIGS. 1A-1D show a cartoons of glycosylated antibodies and the mass distribution of glycosylated and deglycosylated antibody heavy chains determined by mass spectrometry. Partial deglycosylation is demonstrated resulting from standard heat pre-treatment prior to the addition of PNGase F (New England Biolabs, Ipswich, Mass.) (also see Example 1). In the absence of surfactants.

Embodiments of the invention provide improved methods and compositions for analyzing glycoproteins such as antibodies by complete and optionally rapid removal of glycans permitting the separate analysis without bias of the deglycosylated proteins and the released glycans and/or the preparation of functional deglycosylated antibodies.

The advantages of present embodiments include at least one of the following: (i) deglycosylation conditions that minimize oxidation, deamidation, and other unwanted chemical modifications of the protein or the glycans; (ii) deglycosylation conditions that do not interfere with downstream analysis using mass spectrometry; (iii) complete deglycosylation that results in elimination of bias towards certain species of glycans; (iv) rapid reaction conditions that are convenient and cost effective; (v) preservation of function of the deglycosylated proteins; (vi) degradation of protein into peptides with protease and deglycosylation with a glycosidase in a single step; (vii) use of reduced amounts of glycosidase in a reaction and (viii) availability of lyophilized reagents for deglycosylation suitable for adding to the glycosylated antibody. These advantages accrue as a result of certain features of embodiments of the invention. These include one or more of the following: a lyophilized or solubilized preparation of a glycosidase in a dialyzable non-cleavable carboxylated anionic surfactant and/or a bile salt in a buffer. The preparation may additionally contain a reducing agent. The preparation may additionally contain a protease such as trypsin. The preparation may be a solubilized or lyophilized preparation. When combined with a glycosylated antibody, the preparation can achieve complete deglycosylation of a glycosylated antibody in less than 60 minutes at a temperature of less than 70° C. and optionally within a single step reaction or in two-steps involving a pretreatment or in more than two-steps as desired.

The high sensitivity of embodiments of the methods can be used for determining all or substantially all antibody glycoforms present in a sample in a simple, effective, comprehensive and rapid manner. Since substantially all glycans can be removed from a glycoprotein, the inherent bias found in other methods is avoided. The sensitivity also means that less sample can be used. The methods can avoid sample loss arising from multiple handling steps (e.g., heat denaturation, alkylation, SDS treatment where the SDS cannot readily be removed, or the inactivation of heat-labile or acid-labile reagents) normally found in other procedures. Consequently the methods are suitable for low volume or low concentration of samples. Additionally, since embodiments of the methods utilize relatively small amounts of glycosidases, large sample volumes of sample and/or multiple samples (either simultaneously or sequentially) can be readily deglycosylated.

The methods are readily combined with downstream analyses, such as chromatography (e.g., HPLC, HP anion-exchange chromatography with pulsed amperometric detection (HPAE-PAD), gel electrophoresis, mass spectrometry (e.g., MALDI-TOF MS, ESI-TOF MS), and capillary electrophoresis. The methods can be used, for example, to determine the molecular weights, charge state, oxidation, clipping, and deamidation of the deglycosylated proteins (e.g. antibodies), confirm protein deglycosylation (antibody deglycosylation), determine protein function (e.g. antibody function), determine glycan composition, determine glycan structure, and identify glycoprofile information. This facilitates a rapid workflow that has practical implications in the industry. The methods and reagents described herein can be used in diagnostics, quality control, management and process optimization of antibody production (such a therapeutic antibodies), glycomics profiling, and high throughput analyses.

In one embodiments, the substrate glycoprotein is an antibody. In one embodiment, the glycans are N-glycans removable by a PNGase glycosidase.

Unless defined otherwise, all technical and scientific terms used herein have the same meaning as commonly understood by one of ordinary skill in the pertinent art. The scope of certain terms is provided below. Embodiments described herein may include one or more ranges of values (e.g., size, concentration, time, temperature). A range of values will be understood to include all values within the range, including subset(s) of values in the recited range, to a tenth of the unit of the lower limit unless the context clearly dictates otherwise.

As used herein, the articles "a", "an", and "the" relate equivalently to a meaning as singular or plural unless the context dictates otherwise.

The term "antibody" is used interchangeably with the term immunoglobulin and include whole antibodies and fragments which when functional, are capable of binding antigen. An antibody may be natural or recombinant, polyclonal, monoclonal, humanized, mammalian (including human, primate, camel, porcine, equine, rodent, bovid), avian, reptilian, fish, (e.g., hagfish, lampreys, bony and cartilaginous fish, including elasmobranchii). The antibody may be derived from an in vivo sample, such as a serum, plasma r blood sample or other body fluid, secreted, excreted or otherwise removed from the host. Alternatively, an antibody may be from an in vitro cell culture. An antibody (e.g., a therapeutic antibody) may be produced in a bioreactor, or in a multicellular host organism (e.g. a cultured crop). An antibody may be a single chain antibody, for example.

The term "antibody" includes all classes and isotypes of antibody, and include heavy chain Ig, IgA, IgD, IgE, IgG1, IgG2, IgG3, IgG4, IgM, IgNAR, IgW, and IgY and may further include chimeric, multi specific (e.g. bi-specific, tri-specific, tetra-specific), derivatized and fusion proteins thereof. Also included in the definition are recombinant antibodies such as minibody, diabody, triabody, tetrabody, scFv, bi-specific scFv, tri-specific $Fab_3$, single domain antibodies (sdAb), and dual-variable domain antibodies. An antibody fragment that includes Fab, Fab', $F(ab')_2$, Fv, Fc, Fd, single domains (e.g., VhH, $V_L$, $V_H$, $V_{NAR}$), and portions thereof, are included in the term "antibody".

The antibody may be soluble. The antibody may be in an aqueous state or may be precipitated, dried or immobilized for example on a solid surface, such as a bead a column or matrix.

Antibodies including fragments produced by cells are typically glycosylated. Generally, antibodies are glycosylated with N-linked glycans, but they can also contain O-glycans. Glycosylation may occur on any region of an antibody. A particular glycoform of an antibody can vary, depending on a variety of conditions, such as health, disease state or culture conditions. Such variations can impact the activity and half-life of antibodies. An antibody that is deglycosylated may have reduced or no variation in antibody activity or half-life.

In certain embodiments, the affinity between an antibody and an antigen when they are specifically bound in a capture agent/analyte complex is characterized by a $K_D$ (dissociation constant) of less than $10^{-6}$ M, less than $10^{-7}$ M, less than $10^{-8}$ M, less than $10^{-9}$ M, less than $10^{-9}$ M, less than $10^{-11}$ M, or less than about $10^{-12}$ M or less.

The term "glycan" refers to any sugar, in free form or attached to another molecule and includes O-glycans and N-glycans. An N-linked glycan is a glycan covalently linked to an asparagine residue of a polypeptide chain in the consensus sequence: -Asn-X-Ser/Thr, where X is any amino acid except proline. An O-linked glycan is a glycan linked via a glycosidic bond to the hydroxyl group of serine or threonine. The glycan may be a monosaccharide, oligosaccharide or polysaccharide, linear, branched or a mixture of linear and branched chains and composed of a single type of sugar or multiple types of sugars. The term "glycoforms" refers to the different molecular forms of a glycoprotein, resulting from variable glycan structure and/or glycan attachment site occupancy. The term "glycoprofile" refers to the properties or characteristics of glycans on one or more glycomolecules. The profile may include the identity, structure, composition and/or quantity of any one or more glycans, the glycosylation site(s) or location(s) on a glycomolecule, and/or glycan occupancy on a glycomolecule. "Glycoprofile" can be used interchangeably with "glycosylation profile."

The term "glycosylation" refers to the covalent attachment of a carbohydrate to a polypeptide, lipid, polynucleotide or another carbohydrate. The terms "glycosylated peptide" "glycosylated polypeptide" or "glycosylated protein" can be used interchangeably with "glycopeptide," "glycopolypeptide" or "glycoprotein."

The term "deglycosylation" refers to the removal of glycans from a glycan-containing molecule. Deglycosylation can be done enzymatically or chemically. Single glycosidases or mixtures of glysidases may be used to deglycosylate a protein. Cleaving "substantially all" glycans results in a completely deglycosylated protein where "Complete deglycosylation" refers to >70%, >80%, >90%, >92%, >94%, >96%, >98% or >99% deglycosylation by a glycosidase as determined by SDS-PAGE or by mass spectrometry. For example, complete deglycosylation by an N-glycan or an O-glycan glycosidase refers to >70%, >80%, >90%, >92%, >94%, >96%, >98% or >99% N- or O-glycan deglycosylation. If complete deglycosylation is achieved by a mixture of N-glycan and O-glycan glycosidases then this refers to >70%, >80%, >90%, >92%, >94%, >96%, >98% or >99% N-glycan and O-glycan deglycosylation. An example of complete deglycosylation is 90%-100% deglycosylation.

The term "glycosidase" refers to an enzyme that can cleave a glycan and includes endoglycosidases, exoglycosidases, and amidases. In one embodiment, the glycosidase is an endoglycosidase and/or an exoglycosidase. In one embodiment, the glycosidase is an amidase. In some embodiments, the glycosidase cleaves N-linked glycans. In some embodiments, the glycosidase cleaves O-linked glycans. In some embodiments, the glycosidase is selected from the group consisting of deglycosylated peptide-N-glycosidase from almonds (PNGase A) (see below) or from rice (PNGase Ar) (see below), peptide-N-glycosidase F (PNGase F), PNGase Y (Swiss Prot: Q6CAX5.1 YALI0C23562g YALI0C23562p [Yarrowia lipolytica CLIB122] Gene ID: 2909617 NCBI Reference Sequence: NC_006069.1. O-glycosidase (New England Biolabs, Ipswich Mass.), endoglycosidase D (Endo D) (New England Biolabs, Ipswich Mass.), endoglycosidase F (Endo F) (QAbio, Palm Desert, Calif.), endoglycosidase F1 (Endo F1) (QAbio, Palm Desert, Calif.), endoglycosidase F2 (Endo F2) (QAbio, Palm Desert, Calif.), endoglycosidase F3 (Endo F3) (QAbio, Palm Desert, Calif.), endoglycosidase H (Endo H) (New England Biolabs, Ipswich Mass.), endoglycosidase M (Endo M) (TCI America), endoglycosidase S (Endo S) (New England Biolabs, Ipswich Mass.), beta1-3 galactosidase (New England Biolabs, Ipswich Mass.), beta1-4 galactosidase (New England Biolabs, Ipswich Mass.), alpha1-3,6 galactosidase (New England Biolabs, Ipswich Mass.), beta-N-acetylglucosaminidase (New England Biolabs, Ipswich Mass.), alpha-N-acetylgalactosamindiase (New England Biolabs, Ipswich Mass.), beta-N-acetylhexosaminidase (New England Biolabs, Ipswich Mass.), alpha1-2,3 mannosidase (New England Biolabs, Ipswich Mass.), alpha1-6 mannosidase (New England Biolabs, Ipswich Mass.), neuraminidase (New England Biolabs, Ipswich Mass.), alpha2-3 neuraminidase (New England Biolabs, Ipswich Mass.), alpha1-2 fucosidase (New England Biolabs, Ipswich Mass.), or a combination thereof. In some embodiments, the glycosidase is a fusion protein. In some embodiments, the glycosidase is PNGase F. PNGase F is a commercially available enzyme (e.g., New England Biolabs, Ipswich Mass., Cat. #P0704 or #P0710). In some embodiments, the PNGase F is a fusion protein. For example, the PNGase F may be PNGase F tagged with a chitin binding domain (CBD) or a PNGase F-SNAP fusion protein (see example 16). In some embodiments, the glycosidase is lyophilized. In some embodiments, the glycosidase is a lyophilized PNGase F. In some embodiments, the glycosidase is substantially free of animal-derived reagents.

As described herein, the glycosidase (which includes a single glycosidase or a mixture of glycosidases) may be immobilized on a solid, semi-solid or porous surface. Suitable surfaces for immobilization of glycosidases (such as PNGaseF) include beads, resins, columns, wells, plates, microchips, microfluidic devices, filters and the like. In one embodiment, the glycosidase, such as PNGase F, is immobilized on an agarose or magnetic bead. Immobilization may be achieved by means of a fusion protein (e.g. a PNGaseF fusion protein) where the fusion protein has an affinity for a specific molecule such as CBD for chitin or maltose binding domain for maltose. In one embodiment, the fusion protein comprises a mutant AGT.

In one embodiment, one unit of glycosidase is the amount of enzyme required to remove >95% glycans from 5 μg of mouse monoclonal IgG, for 5 minutes at 50° C. in a 10 μl reaction volume.

In another embodiment, one unit of PNGase F is the amount of enzyme required for complete deglycosylation from 10 μg of denatured RNase B in 1 hour at 37° C. in a total reaction volume of 10 μl.

The term "bile acid" refers to a family of molecules composed of a steroid structure with four rings, a (five to eight atom) carbon side chain terminating in a carboxylic acid, and one or more hydroxyl groups. The four rings are labeled from left to right (as commonly drawn) A, B, C, and D, with the D-ring being smaller by one carbon than the other three. The hydroxyl groups can be in either of two positions, up (or out), termed beta (β; often drawn by convention as a solid line), or down, termed alpha (α; seen as a dashed line). All bile acids have a 3-hydroxyl group, derived from the parent molecule, cholesterol. Bile acids are reviewed in Hofmann, et al., *J. Lipid Res.* 51: 226-46 (2010) and Russell, *Annu. Rev. Biochem.* 72: 137-74 (2003) and include cholic acid, glycocholic acid, taurocholic acid, deoxycholic acid, chenodeoxycholic acid, glycochenodeoxycholic acid, taurochenodeoxycholic acid and lithocholic acid, although many others, including synthetically-made variants of naturally occurring bile acids, are known. A bile acid may be employed as a salt, i.e., as a bile salt.

The term "anionic surfactant" refers to a surfactant that has a negatively charged head, such as a sulfate, sulfonate, phosphate or caboxylate.

The term "non-cleavable carboxylated anionic surfactant" which may be referred to as "detergent" refers to an anionic surfactant that has a carboxylated head, examples of which include, but are not limited to, the alkyl carboxylates (soaps), such as sodium stearate, and LS as well as fluorosurfactants such as perfluorononanoate, perfluorooctanoate (PFOA or PFO). Other carboxylated anionic surfactants are known and further examples are described below. The surfactant/detergent may be rendered inactive by cleavage under mildly acidic conditions where other chemical bonds (i.e. peptide bonds, glycosidic bonds etc. are not affected).

The term "dialyzable" refers to molecules that are able to pass through a dialysis membrane (i.e., a semi-semi-permeable membrane) having a molecular-weight cutoff (MWCO) of 25KD, 50KD, or preferably in the range of 75KD-100KD, thereby retaining >90% of a protein having a molecular mass of at least 10 kDa but not the surfactant.

The term "non-naturally occurring" refers to a composition that does not exist in nature. In the context of a protein, the term "non-naturally occurring" refers to a protein that has an amino acid sequence and/or a post-translational modification pattern that is different to the protein in its natural state. For example, a non-naturally occurring protein may have one or more amino acid substitutions, deletions or insertions at the N-terminus, the C-terminus and/or between the N- and C-termini of the protein. A "non-naturally occurring" protein may have an amino acid sequence that is different to a naturally occurring amino acid sequence but that that is at least 80%, at least 85%, at least 90%, at least 95%, at least 97%, at least 98% or at least 99% identical to a naturally occurring amino acid sequence. In certain cases, a non-naturally occurring protein may contain an N-terminal methionine or may lack one or more post-translational modifications (e.g., glycosylation, phosphorylation, etc.) if it is produced by a different (e.g., bacterial) cell.

In the context of a preparation, the term "non-naturally occurring" refers to: a) a combination of components that are not combined by nature, e.g., because they are at different locations, in different cells or different cell compartments; b) a combination of components that have relative concentrations that are not found in nature; c) a combination that lacks something that is usually associated with one of the components in nature; e) a combination that is in a form that not found in nature, e.g., dried, freeze dried, crystalline, aqueous; and/or d) a combination that contains a component that is not found in nature. For example, a preparation may contain a buffering agent (e.g., Tris, HEPES, TAPS, MOPS, tricine or MES), a detergent, a dye, a reaction enhancer or inhibitor, an oxidizing agent, a reducing agent, a solvent or a preservative that is not found in nature. In present embodiments, two-step reactions and one-step reactions are described for deglycosylation under conditions that (a) preserve the binding properties of an antibody for its antigen; (b) preserve the characteristics of the protein or glycan for further analysis; and/or (c) preserve the multimeric structure of the protein if such exists. In some circumstances, a one pot, two-step reaction is sufficient. However, a one-step reaction can facilitate high through-put analysis of glycoproteins and can minimize handling error. Present aspects of the method are effective for nanogram to microgram amounts of glycosylated protein. The successful application of aspects of the method to relatively large amount of substrate protein has utility in detecting rare species of glycans.

A "two-step" procedure includes a first step (the pretreatment step) that, without wishing to be limited by theory, is believed to cause the substrate glycoprotein to become relaxed under conditions that avoid aggregation and/or coagulation of the glycoprotein. The second step (the deglycosylation reaction step/reaction step) utilizes the same or similar buffers as in the first step for convenience and maximum activity of the glycosidase. Here a glycosidase reagent is added for cleavage of the glycans. In contrast, the "one-step" procedure introduces the glycosidase in a master mix at the outset. The one-step procedure preferably utilizes a reducing agent such as DTT that is optional and can be omitted in the two-step procedure. For example, see Example 7 which describes one pot methods using a single step to deglycosylate a protein where an antibody was incubated with a reducing agent, a buffer comprising SDC or LS, and PNGase F. Incubation of the mixture for 5 minutes at 50° C. produced a substantially deglycosylated antibody (see FIG. 7A). Deglycosylation was observed in less than 3 minutes (see Example 9, and FIG. 9).

The pH conditions for the two-step and the one-step methods are similar and are in the range of 4 to 10 for optimal glycosidase activity. For example, the pH may be about 4.0, 4.5, 5.0, 5.5, 6.0, 6.5, 7.0, 7.5, 8.0, 8.5, 9.0, 9.5, 10.0 or any range thereof.

The detergent, SDS was found to be unsuitable in the present embodiments as it denatures the glycoprotein so that it loses any structure or function it might otherwise have. Moreover, SDS cannot be readily removed from the reaction mix and it associates intimately with the protein, and thereafter interferes with mass spectrometry of the glycans and proteins. In the examples, it was found that SDS negatively impacts the activity of glycosidases such as PNGaseF. Therefore SDS was excluded from the present embodiments.

Here it has been found that surfactants such as dialyzable non-cleavable carboxylated anionic surfactants and/or bile acid or salts thereof are suitable for use in the present methods. Without being limited by theory it is believed that non-cleavable, dialyzable carboxylated anionic surfactants or bile acid serve to relax the protein structure and facilitate enzyme mediated deglycosylation. In addition, these reagents can be removed so as not to unduly inhibiting mass spectrometry analysis and may further permit the protein (such as the antibody) to retain the function as demonstrated herein.

Examples of dialyzable, non-cleavable carboxylated anionic surfactant for use in present embodiments include LS, lauric acid, stearic acid, palmitic acid, a combination thereof, and salts thereof. In some embodiments, the carboxylated anionic surfactant salt is LS. The carboxylated anionic surfactant may be lyophilized and/or may be substantially free of animal-derived reagents.

Whereas it is possible to use a range of concentrations of the dialyzable, non-cleavable carboxylated anionic surfactant such as sodium LS or SDC, it is preferable to use a concentration of at least 0.5%, e.g., a concentration in the range of 0.5% to 8% or a concentration in the range of 1% to 5%.

Examples of bile acid for use in present embodiments include cholic acid, chenodeoxycholic acid, lithocholic acid, deoxycholic acid, ursodeoxycholic acid or salts thereof or a combinations of the foregoing. In some embodiments, the bile acid is deoxycholic acid. In one embodiment, the bile acid salt is SDC. The bile acid may be lyophilized. The bile acid may be substantially free of animal-derived reagents. Whereas it is possible to use a range of concentrations of a bile salt such as SDC, it is preferable to use a concentration of at least 2% such as 3% or 5%. In one embodiment SDC is used at a concentration of about 2%.

Further examples of detergents suitable for use as described herein may be obtained from Sigma Life Sciences (see Biofiles (2008) Vol. 3 No. 3 "Detergents and Solubilization reagents"), G-Biosciences "Detergents: A handbook and Selection Guide to Detergents and Detergent Removal".

In addition to the anionic carboxylic surfactants and/or bile salts, it has been found to be advantageous but not essential to include a reducing agent to the deglycosylation pretreatment or reaction mixture.

In some embodiments, the reducing agent is DTT, β-mercaptoethanol, or TCEP. The final concentration of the reducing agent can be determined by those of skill in the art. In some embodiments the reducing agent is DTT. For example, the final concentration of DTT may be between about 0.2 mM to about 100 mM. For example, the final concentration may be about 0.2 mM, 0.4 mM, 0.6 mM, 0.8 mM, 1 mM, 2 mM, 5 mM, 10 mM, 15 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, 100 mM, DTT, or any range thereof (see Example 4 and 5). In some embodiments, the reducing agent is TCEP. In some embodiments, the final concentration of TCEP is between about 0.2 mM to about 10 mM. For example, about 0.2 mM, 0.4 mM, 0.6 mM, 0.8 mM, 1 mM, 2 mM, 5 mM, 10 mM TCEP, or any range thereof (see Example 6).

In one embodiment, a glycoprotein can be optionally pre-treated before deglycosylation where the entire deglycosylation reaction may be completed in less than 60 minutes such as less than 30 minutes. In some embodiments, the deglycosylation reaction mixture (either with or without a heat pre-treatment) is incubated at a temperature of about 25° C. to as high as 70° C. (e.g., about 25° C., 30° C., 37° C., 40° C., 43° C., 45° C., 48° C., 50° C., 53° C., 55° C., 58° C., 60° C., 63° C., 65° C., 70° C. or a range thereof) for about 2 minutes, 3 minutes, 4 minutes, 5 minutes, 10 minutes, 15 minutes, 30 minutes, 1 hour, 2 hours, 5 hours, 10 hours, or any range thereof. See for example, Example 7. In one embodiment, the mixture is incubated at about 37° C., 45° C., or 50° C. for about 30 minutes, 15 minutes, 10 minutes, 5 minutes or for about 3 minutes or less. In some embodiments, the reaction may be at least 90% complete in 2 minutes to 60 minutes at a temperature in the range of 30° C. to 50° C. The reaction conditions, e.g., the temperature, may vary depending on the enzyme used.

The concentration of the antibody in the reaction may be in the range of 10 ng/μl to 10 μg/μl, e.g., 100 ng/μl to 5 μg/μl, although concentrations outside of this range are envisioned.

In certain embodiments, a mixture that contains antibodies that are pre-treated with surfactants without glycosidase at a temperature of about 45° C. to about 95° C. for 1 minute to 60 minutes, e.g., about 1 minute, 2 minutes, 3 minutes, or less than about 5 minutes, 10 minutes, 15 minutes, or 30 minutes, before adding the glycosidase results in substantially complete deglycosylation after addition of the glycosidase. This is shown in, for example, Examples 7, and 17. In one embodiment, the pre-treatment incubation is about 15 minutes at about 55° C. In another embodiment, the pre-treatment incubation is about 2 minutes at about 80° C. (see for example, FIGS. 7A-7B, FIG. 8, Example 7 and Example 8 demonstrating various ranges of suitable temperatures for deglycosylation from ambient (room) temperature to about 63° C.). In other examples, a glycosylated antibody can be optionally pre-treated with a reducing agent such as DTT and a buffer comprising a dialyzable, non-cleavable carboxylated anionic detergent such as LS or a bile acid such as SDC before incubation with the glycosidase.

The Examples demonstrate deglycosylation of antibodies in less than 60 minutes, 30 minutes, 15 minutes, 5 minutes, 4 minutes and 3 minutes. Complete deglycosylation can be achieved at a temperature in the range of room temperature to about 55° C. for 5 minutes. By way of an example, a temperature of 55° C. may be used for 10 minutes or a temperature of 37° C. may be used for 15 minutes which in combination with the a dialyzable, non-soluble carboxylated anionic detergent or a bile acid results in sufficient opening of the substrate glycoprotein to permit access to the glycans for cleavage.

Figure 8:
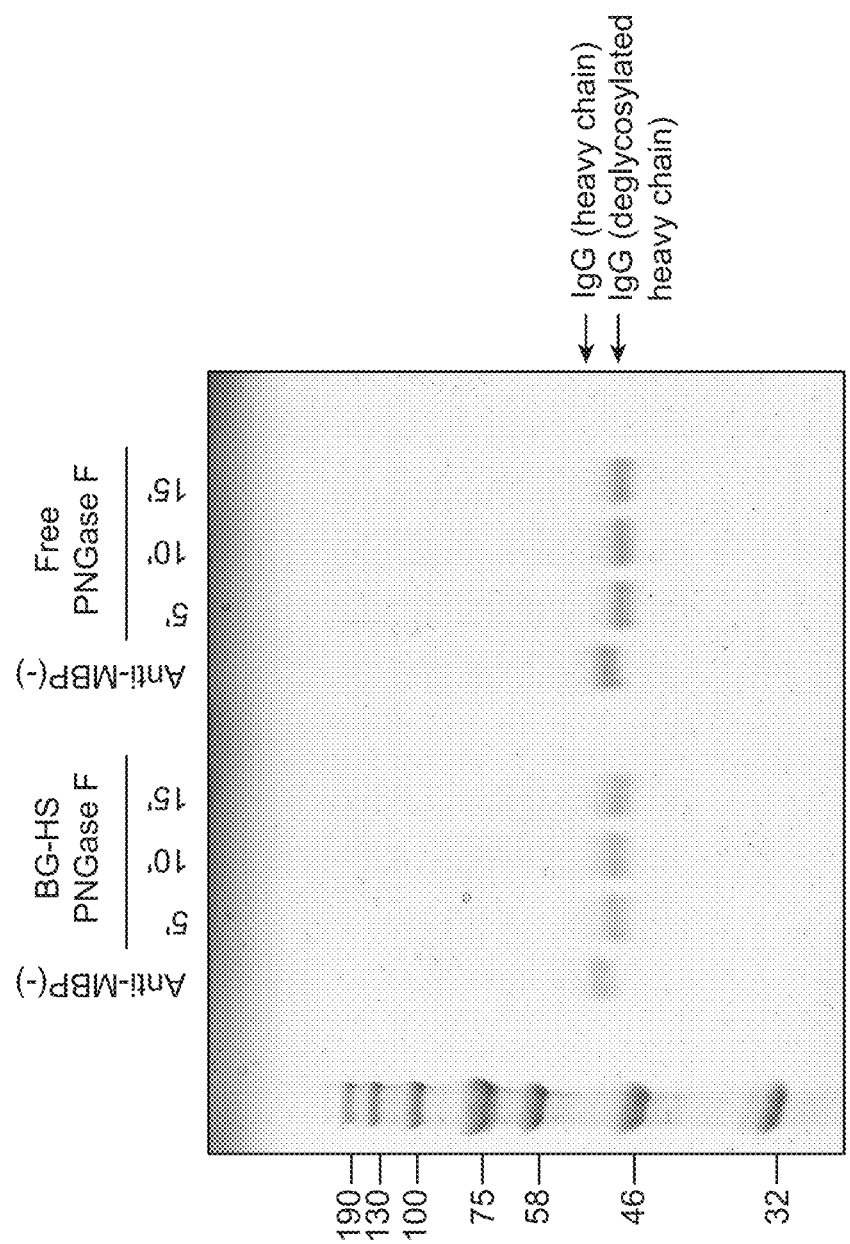
FIG. 8 demonstrates deglycosylation of murine anti-maltose binding protein (anti-MBP) at 22° C. comparing immobilized PNGase (Benzyl-Guanine—mutant AGT (BG-HS) PNGase F) and soluble (Free) PNGaseF with a 5 minute, 10 minute and 15 minute incubation. The results in FIG. 8 shows complete antibody deglycosylation in a two-step reaction, after incubation for 5 minutes at room temperature with immobilized PNGase F as well as with soluble PNGaseF (see also Example 8).

In some embodiments, it is desirable to deglycosylate an antibody at ambient temperatures (about 22° C.). It was an unexpected finding that deglycosylation of an antibody in the mixture could still be rapid. In one embodiment, the mixture is incubated at an ambient temperature for about 2 minutes, 3 minutes, 4 minutes, 5 minutes, 10 minutes, 15 minutes, 30 minutes, 1 hour, 2 hours, 5 hours, 10 hours, or a range thereof. Example 8 and FIG. 8, show rapid deglycosylation in 15 minutes, 10 minutes, 5 minutes or less using an immobilized PNGase F or free PNGase F (either with or without a pre-treatment) at ambient temperature. In one embodiment, the ambient temperature is about 18° C. to about 25° C. (e.g., about 18° C., 19° C., 20° C., 21° C., 22° C., 23° C., 24° C., 25° C., or a range thereof). Immobilized PNGase F may be preferably used at ambient temperatures for reasons other than enzyme activity. However the immobilized PNGaseF may also be used at any of the higher temperatures described herein.

Determining which glycoforms are present in an antibody sample is useful in determining whether the antibody will have an expected activity and/or half-life depending on the specific glycoform that is present. The present methods are effective for deglycosylation of glycoforms.

Deglycosylation at ambient temperatures (as shown herein (see Example 16) is particularly desirable for in-line production or analytical processes. Ambient temperature deglycosylation is one particular application of using immobilized PNGase F in the methods described herein.

In one embodiment, the deglycosylated antibody is separated (isolated, purified) from the cleaved glycans. For example, the separation methods can include protein A affinity chromatography, protein G affinity chromatography, protein L affinity chromatography, etc. Additional separation methods include use of a universal N-glycan binding reagent, such as described in U.S. Provisional Ser. No. 62/020,335, filed Jul. 2, 2014, the teachings of which are incorporated herein by reference in their entirety.

The glycoforms can be determined using any standard techniques, such as chromatography, electrophoresis, spectrometry or mass spectrometry. In Example 14, the glycoforms were determined by mass spectrometry.

In one embodiment, the deglycosylated antibody or deglycosylated fragment thereof, and/or the cleaved glycans are labeled. Labels are art-standard and a non-exhaustive list includes fluorescent label, radioisoptope, methyl acetyl, an antibody, or a combination thereof. In one embodiment, cleaved glycans are labeled with 2-aminobenzamide (2-AB). Alternatively, or in combination with 2-AB, cleaved glycans can be labeled with 2-aminobenzoic acid (anthranilic acid; 2-AA). Advantageously, the methods described above are compatible with direct labeling of the products without the need for prior purification of the products from the mixture. Illustrative examples of this embodiment are described in Examples 11 and 12. Furthermore, labeling of the glycans can be achieved under high aqueous conditions. High aqueous conditions refers to a solution having at least or about 60%, 65%, 70%, 75%, 80% or 85% (vol/vol) water. In one embodiment, the glycans are labeled in the presence of at least 80% water.

In one embodiment, methods further comprise incubating the mixture with a labeling reagent at a temperature of about 55° C. to about 75° C. for about 30 minutes to about 3 hours. In one embodiment, the mixture is incubated with a labeling reagent for about 30 minutes, 45 minutes, 1 hour, 1.5 hours, 2 hours, or 3 hours. In one embodiment the mixture is incubated with a labeling reagent at about 55° C., 65° C., 65° C., 70° C., or 75° C. In one embodiment, the mixture is incubated with a labeling reagent at about 65° C. for about 2 hours. Examples of labeling agents include fluorimetric dyes such as fluorescein isothiocyanate, tetramethylrohodamine isothiocyante, lissamine rhodamine B, naphthaline-5-sulfonic acid, Alexa Fluor® dyes (488, 546, 555, 568, 594, 647, 350, 532), Qdot® fluorophores, Pacific Blue™, Pacific Orange™, and Oregon Green® (all commercially available from Life Technologies, Carlsbad, Calif.).

Substantially all glycans can be removed from a glycoprotein in an unbiased manner. By way of example, N-linked glycans may be cleaved from an antibody, isolated and labeled for analysis. In Example 16, samples were analyzed by LC/ESI-MS. The released glycans may be labeled with or without prior isolation of the released glycans (e.g. as illustrated in Example 16). As further described in Example 11, substantially all N-linked glycans may be cleaved and either isolated before labeling in a two-pot method (illustrated in FIG. 11B), or directly labeled without isolation in a one pot method (illustrated in FIG. 11A). The overall profile of labeled glycans was identical whether the glycans were first isolated or not. However, the absolute quantities of glycans was significantly increased in the one pot method. In these embodiments, the glycans may be cleaved from a glycosylated antibody (such as monoclonal IgG antibody) using a glycosidase (such as PNGase F) in the presence of DTT and SDC. Similar deglycosylation results were also demonstrated using a dialyzable, non-cleavable carboxylated anionic surfactant, exemplified by LS, in a one-pot deglycosylation and labeling method (see Example 12 and FIGS. 12A-12C). This demonstrates the unexpected compatibility of a glycosidase reaction comprising bile salts or carboxylated surfactants with direct labeling of the glycans which minimize antibody precipitation during glycan labeling.

In one embodiment, the deglycosylated antibody retains at least 75%, 80%, 85%, 90%, 95%, 99% or 100% epitope binding avidity and/or affinity compared to the epitope binding avidity and/or affinity of the corresponding glycosylated antibody tested under identical reaction conditions. Epitope binding avidity and/or affinity can be confirmed using art standard techniques, such as western blot, ELISA, Biacore, etc. For example, an antibody was completely deglycosylated and the its activity was confirmed by a western blot to retain epitope binding (see Example 13 and 19, FIGS. 13C and 18C). Embodiments of the methods can be applied to any glycosylated antibody class or isotype. As shown in Examples 13 and 15, all antibodies can be successfully deglycosylated to a substantially deglycosylated form (see also FIGS. 13A-13C, and FIGS. 15A-15B).

In one embodiment, a protease such as trypsin can be added to a reaction mixture containing a glycosidase such as PNGaseF without substantial loss of activity of the glycosidase. The protease can cleave the antibody into peptide fragments while the glycosidase removes the glycans in a single reaction. Examples of suitable proteases include: Trypsin, GluC, AspN, proteinase K, Factor Xa, Enterokinase (New England Biolabs, Ipswich, Mass.), LysC, Arg-C, (Promega, Madison, Wis.), LysN (Life Technologies, Carlsbad, Calif.), IdeS (Genovis, Cambridge, Mass.), V-8 Protease, Papain, Alpha-Lytic Protease, Pyroglutamate Aminopeptidas, Leucine Aminopeptidase, Methionine Aminopeptidase, Aminopeptidase I, Aminopeptidase A, Carboxypeptidases (A, B, G, Y), pepsin, Cathepsins (B, C, D), α-Chymotrypsin (Sigma-Aldrich, St. Louis, Mo.), TEV, Thrombin, IdeZ and IdeE (New England Biolabs, Ipswich, Mass.).

In one embodiment, reactants may be lyophilized before use without negatively affecting deglycosylation.

Also provided is a kit. In one embodiment, the kit comprises one or more lyophilized reagents. In one embodiment, the lyophilized reagent is selected from the group consisting of: lyophilized glycosidase such as lyophilized PNGase F; a lyophilized buffer, wherein the buffer comprises a bile acid, or a salt thereof, a carboxylated anionic surfactant, or a salt thereof, or a combination thereof; a lyophilized reducing agent; and a combination thereof. Bile salts, dialyzable, non-cleavable carboxylate anionic surfactants, and salts thereof are described above. Additionally or alternatively, the kit comprises an immobilized glycosidase such as PNGase F. Illustrative lyophilized reagents, immobilized PNGase F, and methods of using them are described in the Examples (see Examples 8 and 14). In one embodiment, the kit further comprises one or more components selected from the group consisting of a glycan labeling reagent, a control standard, and instructions for use. In one embodiment, one or more reagents are substantially free of animal-derived products. In another embodiment a protease may be included in the kit, for example trypsin where the protease may be lyophilized with the glycosidase and/or the reaction buffer or separately.

Examples of reagents and methods for preparing a deglycosylated protein illustrated herein by an antibody or deglycosylated fragment thereof are not intended to be limiting but rather illustrate embodiments of the invention. Embodiments are applicable to any glycosylated protein not limited to antibodies including antibody fragments. Examples of reagents and methods for obtaining substantially all linked glycans from a glycoprotein are the result of in vitro analysis and do not constitute nor can be construed nor intended as naturally occurring mixtures or events such as might occur in vivo. Embodiments of the deglycosylation methods are compatible with the direct labeling of the glycans cleaved from proteins such as antibodies including fragments thereof without prior purification of the glycans from a mixture comprising the antibody or fragments thereof and the glycan. Alternatively, deglycosylated proteins such as antibodies including deglycosylated fragments thereof can be further processed before proteomic analysis by any suitable means, including dialysis, drop dialysis, filtration with molecular sieves, or solid phase extraction. Glycans can also be further processed, if desired, by for example, solid phase extraction with normal or reverse phase (C18, graphite carbon, HILIC). Also provided are methods and reagents that facilitate sample processing at ambient temperatures. Such methods and reagents are particularly useful for in-line sample analyses in industrial production applications.

Below is a description of a novel modified PNGase derived from almonds which cleaves alpha 1,3 fucose suitable for removing N-glycans from proteins made recombinantly in plants, insects, mollusks and helminthes. These glyco-epitopes are absent in humans as well as other vertebrates and as such have been implicated in allergenic and immunogenic responses in humans and may be a factor for rapid clearance of the plant or insect derived recombinant therapeutic protein (Bardor, et al., *Current Opinion Structural Bio.* 16:576-583 (2006)). The almond derived glycosidase is found in nature as an N-glycosylated heterodimer. In embodiments of the invention, it is used as a single chain deglycosylated polypeptide. It was found to be similarly effective as other glycosidases in preparations described in the examples for PNGaseF.

TABLE 1

Examples of plant derived glycosidases (PNGases)

| Source | Genbank Accession # |
| --- | --- |
| *Prunus dulcis* (Almond) | P81898 |
| *Populus trichocarpa* (Black cottonwood) | XP_002316856, XP_002316193, XP_002311245 |
| *Vitus vinifera* (Common grape) | XP_002285454, CAN82504, XP_002283158, CBI20191, CAN82508, CBI25436, XP_002273437, CAN73340 |
| *Ricinus communis* (Caster oil plant) | XP_002524519, XP_002520774 |
| *Glycine max* (Soybean) | XP_003525973, XP_003541051, XP_003545222, XP_003519424 |
| *Solanum lycopersicum* (Tomato) | NP_001234709 |
| *Medicago truncatula* (Barrel Medic) | XP_003589332, XP_003616684 |
| *Arabidopsis thaliana* | NP_188110, NP_568155 |
| *Thellungiella halophila* | BAJ33648 |
| *Sorghum bicolor* | XP_002454968, XP_002454967, XP_002457153, XP_002454965, XP_002454966, XP_002441054 |
| *Oryza sativa Indica* Group | EEC79173 |
| *Oryza sativa Japonica* Group (Rice) | NP_001042348, EAZ10975, NP_001042351, BAB92157, EAZ10974, NP_001042356, EEE54084, NP_001055461 |
| *Arabidopsis lyrata* subsp. *lyrata* | XP_002873210 |
| *Brachypodium distachyon* (purple false brome) | XP_003565482, XP_003565481, XP_003565312, XP_00356851 |
| *Hordeum vulgare* subsp. *vulgare* (Barley) | BAK07800, BAJ92852, BAJ99566, BAJ91834, BAJ89900, BAJ93147 |
| *Picea sitchensis* (Sitka spruce) | ABK25189 |
| *Zea mays* (Corn) | NP_001152324, NP_001142407, ACF88207 |
| *Physcomitrella patens* subsp. *patens* (moss) | XP_001785381, XP_001764866, XP_001760904 |
| *Selaginella moellendorffii* (spikemoss) | XP_002982418, XP_002966580 |

In an embodiment of the invention, a PNGase was used as described above which had at least 85%, 90%, 92%, 93%, 94%, 95%, 96%, 97%, 98% or 99% amino acid sequence homology to the following sequence:

```
                                         (SEQ ID NO: 1)
AAVPHRHRLPSHHLASLKLNASAPPTTYFEVDRPIRPPRGSVGPCSTLLL

SNSFGATYGRPPVTAAYAPPSCLAGGGGGGGASSIALAVLEWSADCRGR

QFDRIFGVWLSGAELLRSCTAEPRATGIVWSVSRDVTRYAALLAEPGEIA

VYLGNLVDSTYTGVYHANLTLHLYFHPAPPPPPPPQQADLIVPISRSLPL

NDGQWFAIQNSTDVQGKRLAIPSNTYRAILEVFVSFHSNDEFWYTNPPNE

YIEANNLSNVPGNGAFREVVVKVNDDIVGAIWPFTVIYTGGVNPLLWRPI

TGIGSFNLPTYDIDITPFLGKLLDGKEHDFGFGVTNALDVWYIDANLHWL

DHKSEETTGSLISYEAQGLVLNVDSGFSGLDGQFVTSASRHISATGLVKS

SYGEVTTNFYQRFSYVNSNVYSKNGSVQVVNQTIDAKSGVFAKDALAVLL

SEELHQIFPLYVYTGTSDEEADEYTLISHVKLGVNEKETSGGKMGFSYNS

LRNAQSAHGSMKVKKNLVVGGLGETHQAYKYVGADGCYFRDVRSKNYTVL

SDHSGDSCTKRNPYNGAKFSLRNDQSARRKLMVNNL.
```

To further enhance properties such as expression levels and activity of the selected PNGase cloned in non-natural host cells, mutations may be targeted to dibasic sites in the protein for example, a basic amino acid could be converted to any other amino acid particularly those observed at the same location in other isoforms from the same organism. Selection of amino acids to substitute for dibasic sites may be made in such a way to avoid disrupting any secondary structures such as a helixes or β sheets. These potential structures are identified by computer programs such as Jpred3 (Cole, et al., Nucleic Acids Research, 36(suppl 2):W197-W201 (2008)).

The selected PNGase was expressed as a single polypeptide in non-cognate host cells and when expressed in animal cells or yeast, baculovirus/insect cells, the recombinant PNGase itself became modified with N-linked glycans.

For ease of purification, a host cell such as yeast capable of secreting PNGase was selected although the PNGase could also be purified from the lysate of the host cells. Examples of suitable host cells for expressing the plant PNGase may include yeast such as *Kluyveromyces lactis* (*K. lactis*) or *Pichia pastoris* (*P. pastoris*). Where the PNGase was synthesized in the nonnative-host cell with a high mannose N-linked glycan, it was preferably deglycosylated using a suitable high mannose N-linked glycans cleavage enzyme such as Endo H.

The activity of the plant PNGase for N-linked glycans containing α1,3 fucose can be determined using any substrate for which the N-linked glycans have been fully described without the need for first cleaving the protein into peptides. For example, HRP and pineapple bromelain have N-linked glycans containing α1,3 fucose that have been fully characterized. Substantially all the glycans on these proteins have an GlcNAc linked to a fucose via an α1,3 glycosidic bond and also to a second GlcNAc linked to two mannoses (bromelain) or three mannoses (HRP) where the first mannose is also linked to a xylose. In contrast, snail hemocyanin and human IgG has a GlcNAc linked to fucose via an α1,6 glycosidic bond. HRP and pineapple bromelain are both useful glycoprotein substrates for assaying for cleavage of N-linked glycans containing α1,3 fucose by glycosidases. These glycoproteins can be readily conjugated to a label that produces a colored or fluorimetric signal. Examples of fluorimetric dyes: fluorescein isothiocyanate, tetramethylrohodamine isothiocyante, lissamine rhodamine B, naphthaline-5-sulfonic acid, Alexa Fluor® dyes (488, 546, 555, 568, 594, 647, 350, 532) Qdot® fluorophores, Pacific™, Pacific Orange™, and Oregon Green®.

The specific activities of the PNGase dipeptide purified from almond and the recombinant monopeptide PNGase Ar cloned from rice and expressed in either *K. lactis* or *P. pastoris* can be as much as 500,000 to 600,000 units/mg of protein. One unit is defined as the amount of enzyme required to remove >95% of the carbohydrate from 10 μg of denatured RNase B in 1 hour at 37° C. in a total reaction volume of 10 μl.

The ability to deglycosylate N-glycans containing α1,3 fucose and to characterize these N-glycans has many uses. These include meeting federal regulation requirements for the characterization of therapeutic proteins. Additionally, removal of the N-glycans can reduce unwanted side effects of administering these therapeutic proteins. Examples of applications are provided below.

HRP produces a colored, fluorimetric, or luminescent derivative of the labeled molecule when incubated with a specific substrate, allowing it to be detected and quantified. HRP is often used in conjugates (molecules that have been joined genetically or chemically) to determine the presence of a molecular target. For example, an antibody conjugated to HRP may be used to detect a small amount of a specific protein in a western blot. To avoid cross-reactivity, antibodies can be prepared against HRP that has been deglycosylated with PNGase using embodiments of the method described herein.

Individualized vaccines have been developed for treatment of lymphomas using proteins. Deglycosylation of these proteins is preferable. A vaccine for non-Hodgkin's lymphoma has been produced in tobacco plants where removal of the N-glycan involves α1,3 fucose (McCormick, et al., PNAS, 105:10131-10136 (2008)). PNGase Ar can be used to analyze whether the activity of the intact deglycosylated protein is equivalent to the glycosylated protein but with the advantages that accrue from deglycosylation.

All references cited herein are incorporated by reference including U.S. Provisional Application Ser. No. 62/005,559, filed May 30, 2014, 62/018,074, filed Jun. 27, 2014, 62/021, 936 filed Jul. 8, 2014, 62/040,745 filed Aug. 22, 2014 and 62/080,480 filed Nov. 17, 2014.

EXAMPLES

Figure 1B:
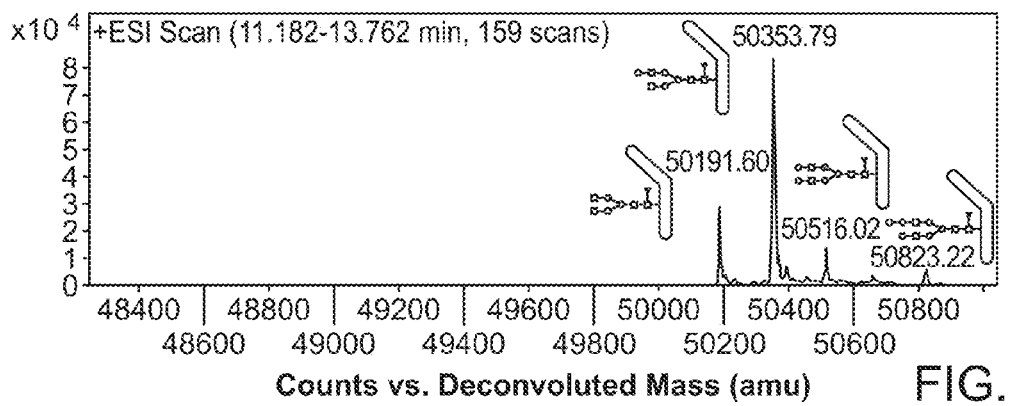
Figure 1C:
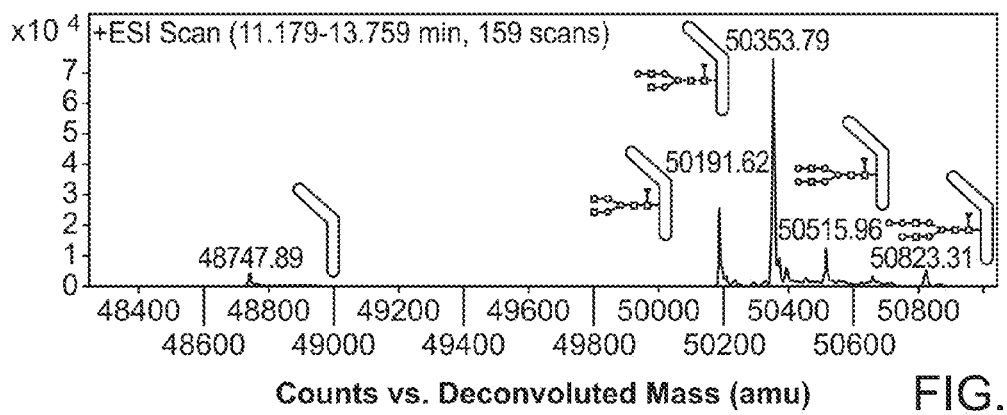
Figure 1D:
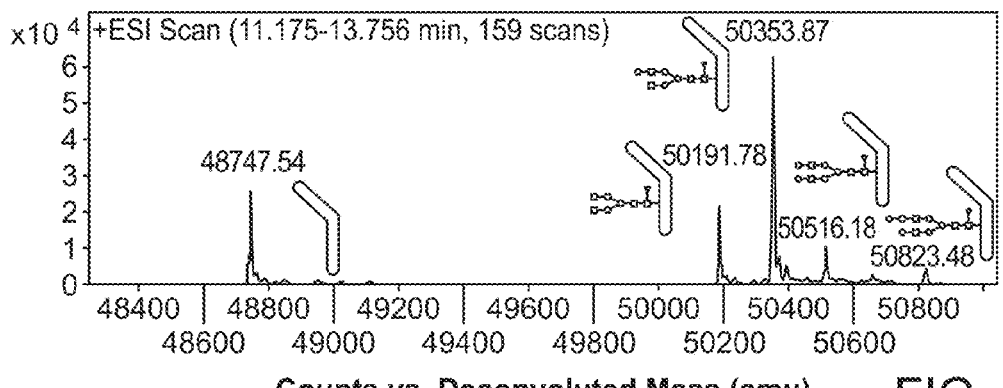

Example 1: Pre-Treatment of an Antibody by Mild Heat Alone Prior to PNGase F Treatment does not Produce a Completely Deglycosylated Antibody Preparations of a concentrated sample of IgG: Aliquots of Anti-MBP Monoclonal Antibody (New England Biolabs, Ipswich, Mass.) were lyophilized and resuspended in 250 µL of water (yielding a final concentration of 4 µg antibody/µL in 200 mM NaCl, 4 mM EDTA, 40 mM Tris pH 7). Concentrated IgG (36 µg) was diluted with water to a total volume of 27 µL. Samples were heated to 55° C. for 10 minutes, and then kept at 4° C. To all samples, 3 µL of detergent free buffer were added. Control reactions did not contain any deglycosylating enzyme, whereas 1 µL of Rapid PNGase F was added to each deglycosylation experimental sample. Reactions were incubated for 1 hour or 16 hours at 37° C. then kept at 4° C. until further analyzed. To determine the intact mass of the IgG by ESI-TOF, the deglycosylated IgG samples were further treated with 10 mM DTT for 30 minutes at room temperature, and formic acid was added to 0.1%. Samples were analyzed by reverse phase liquid chromatography (LC) with PLRP-S (5 µm particles, 1000 A pore size) and electrospray ionization time-of-flight mass spectrometry (ESI-TOF MS) using methods known in the art. Results are shown in FIGS. 1A-1C.

Figure 2A:
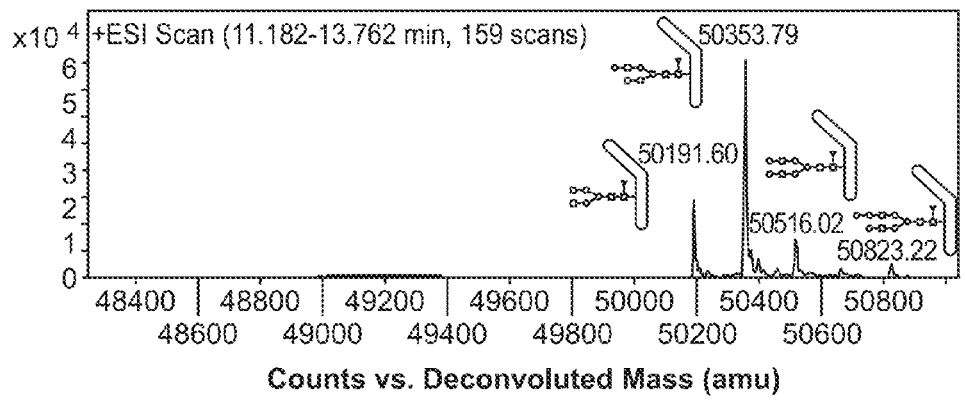
FIGS. 2A-2C show the mass distribution of an antibody heavy chain in mass spectrometry and demonstrate that a stronger pre-treatment of combined heat denaturation and a reducing agent prior to PNGase F treatment is insufficient to produce a substantially deglycosylated antibody (see also Example 2).
Figure 2B:
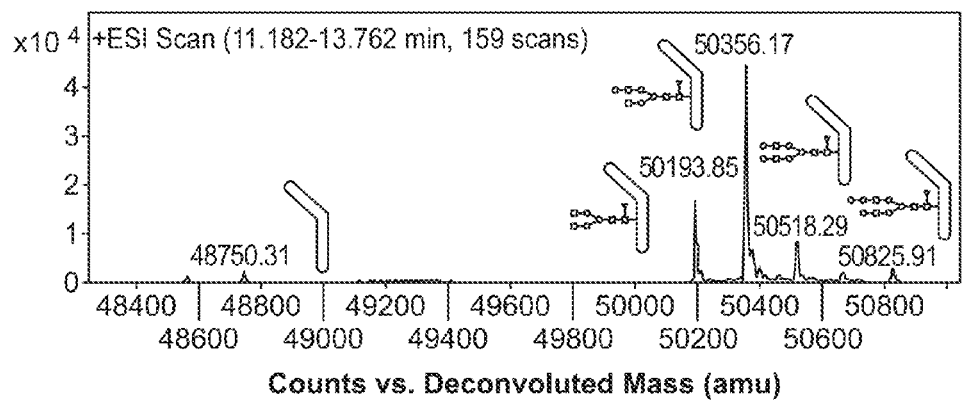
Figure 2C:
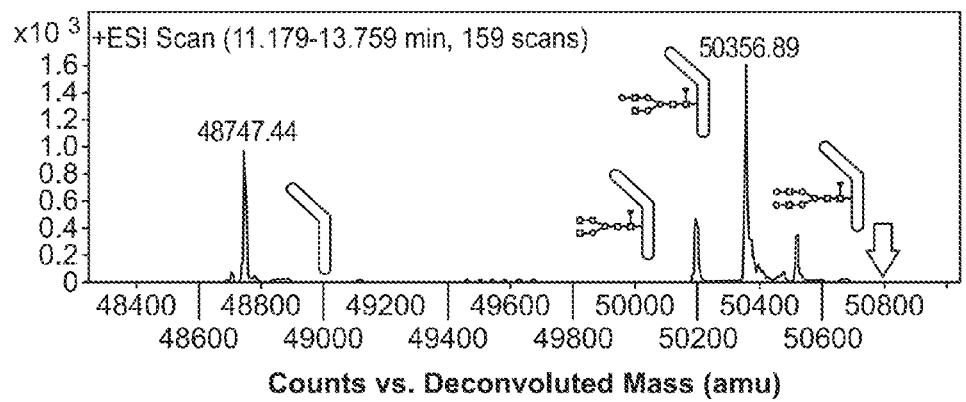

Example 2: Pre-Treatment of an Antibody by Heat Denaturation in Combination with a Reducing Agent Prior to PNGase F Treatment does not Produce Completely Deglycosylated Antibody A concentrated IgG sample was prepared as described in Example 1. The monoclonal IgG (36 µg) was diluted in 40 mM DTT to a volume of 27 µL. Samples were incubated at 55° C. for 10 minutes, after which 3 µL of reaction buffer (500 mM sodium phosphate pH 7.5) were added. Negative controls did not contain any deglycosylating enzyme whereas 500 U of PNGase F Glycerol Free was added to each deglycosylation experimental sample. Reactions were incubated for 1 hour or 16 hours at 37° C. then kept at 4° C. until further analyzed. The intact mass of the detergent-free IgG sample was analyzed by ESI-TOF as described in Example 1. Results are shown in FIGS. 2A-2C.

Figure 3A:
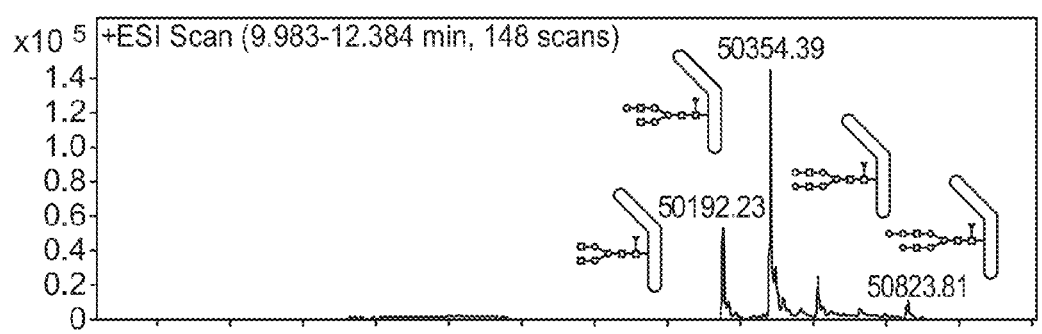
FIGS. 3A-3B demonstrate that an antibody is not substantially deglycosylated after pre-treatment of the antibody using a commercially available reagent, RapiGest™ (Waters, Milford, Mass.) ahead of PNGase F digestion. As described in Example 3, a glycosylated antibody was pre-treated with manufacturer's suggested amount of RapiGest. The pre-treated antibody was incubated with PNGase F for 1 hour before ESI-TOF MS analysis.
Figure 3B:
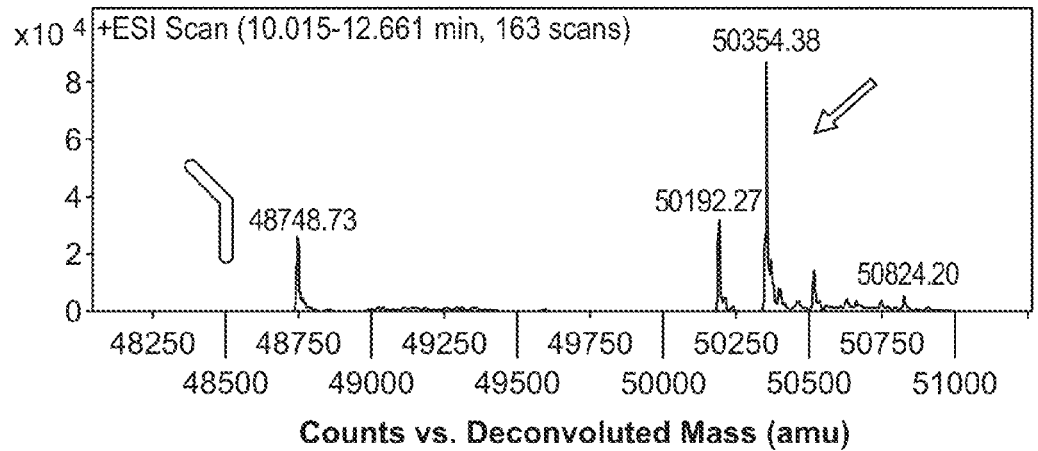

Example 3: Treatment with the Commercial Reagent RapiGest™ Prior to PNGase F Deglycosylation does not Produce Completely Deglycosylated Antibody A concentrated IgG sample was prepared as described in Example 1. Aliquots of monoclonal IgG (64 µg) were rehydrated in 0.1% RapiGest™ in a total volume of 20 µL. Samples were incubated at 55° C. for 10 minutes, after which, 10 µL of reaction buffer. Control reactions did not contain any deglycosylating enzyme, whereas 1 µl of Rapid PNGase F were added to each deglycosylation experimental sample. Reactions were incubated for 1 hour at 37° C. The intact mass of the detergent-free IgG sample was analyzed by ESI-TOF as described in Example 1. Results are shown in FIGS. 3A-3B.

Example 4: Complete Deglycosylation of an Antibody Using a Carboxylated Surfactant in a Range of Concentrations An anti-MBP mouse monoclonal IgG 36 µg, (New England Biolabs, Ipswich, Mass.) was mixed with varying amounts of DTT (final concentration ranging from 0.2 to 80 mM) and varying amounts of LS (final concentration ranging from 0.05 to 5% w/v), in a total volume of 20 µL. Control reactions did not contain any deglycosylating enzyme. 1 µl of Rapid PNGase F was added to all other samples and were incubated for 5 minutes at 50° C. An aliquot of each sample was separated via SDS-PAGE and visualized with SimplyBlue™ SafeStain (Life Technologies, Carlsbad, Calif.).

Figure 4A:
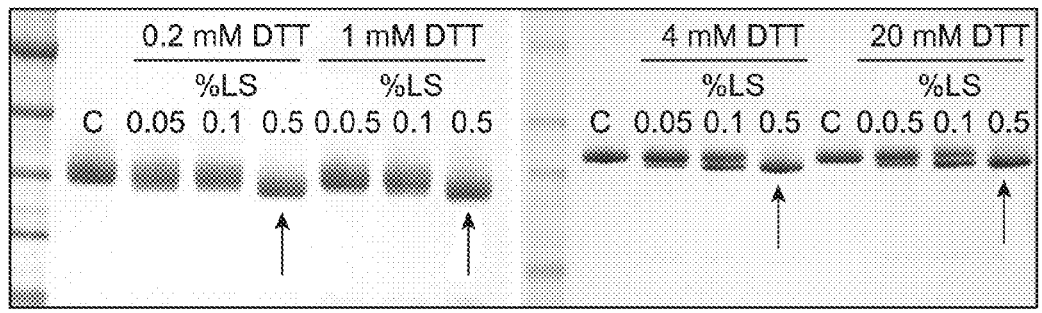
FIGS. 4A-4C show the wide range of conditions in which a carboxylated surfactant lauroylsarcosine (LS), DTT and PNGaseF can produce a substantially deglycosylated antibody in 5 minutes at 50° C. (see also Example 4). Shown are the SDS-PAGE mobility shifts of a mouse monoclonal IgG antibody (New England Biolabs, Ipswich, Mass.) (described in Example 1) after deglycosylation with PNGase F in the presence of varying amounts of LS in combination with varying amounts of DTT. The arrows indicate lanes where complete deglycosylation of the substrate is detected by a shift in the gel position corresponding to a reduction in molecular weight.
Figure 4B:
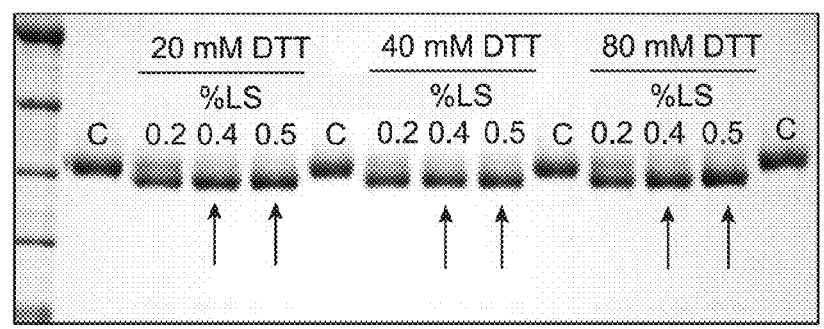
Figure 4C:
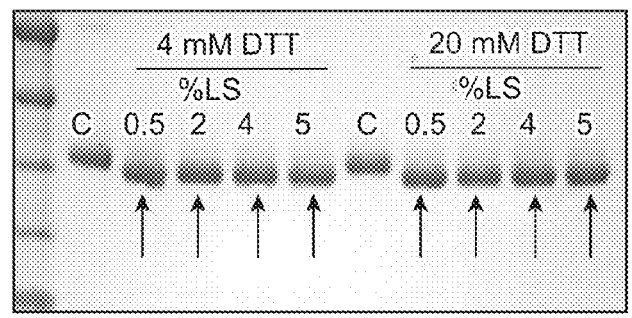
Figure 5:
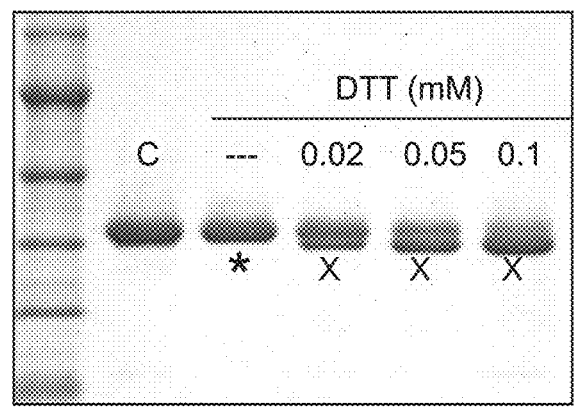
FIG. 5 shows that low concentrations of DTT enhance deglycosylation of antibodies in the presence of 0.5% LS and PNGaseF for an incubation period of 5 minutes at 50° C. (see also Example 5). Mouse monoclonal IgG antibody (described in Example 1) treated with PNGase F in 0.5% LS in combination with 0.02 mM, 0.05 mM or 0.1 mM DTT is shown by SDS-PAGE mobility shifts. Deglycosylation of the substrate was observed by an increase in sample mobility on SDS-PAGE corresponding to a reduction of molecular weight resulting from loss of glycans (see "X").

Similar experiments were repeated using varying concentrations of SDC (e.g., ranging between about 0.05% to about 5% w/v) (data not shown). Deglycosylation was achieved in 5 minutes or less at about 50° C., with or without a heat pre-treatment of the glycosylated sample. Complete deglycosylation was demonstrated in a range of about 2% to 5% SDC. Results are shown in FIGS. 4A-4C.

Example 5: Complete Deglycosylation of an Antibody Using a Range of Concentration of the Reducing Agent DTT An anti-MBP mouse monoclonal IgG (36 µg, New England Biolabs) was mixed with varying amounts of DTT (final concentration ranging from 0 to 0.1 mM) and LS (final concentration 0.5% w/v) in a total volume of 20 µL. Control reactions did not contain any deglycosylating enzyme. 1 µl Rapid PNGase F was added to all other samples and were incubated for 5 minutes at 50° C. An aliquot of each sample was separated via SDS-PAGE and visualized with Simply-Blue SafeStain. Results are shown in FIGS. 5A-5D.

Example 6: Complete Deglycosylation of an Antibody Using a Range of Concentrations of Reducing Agent, tris(2-carboxyethyl)phosphine (TCEP)

Figure 6:
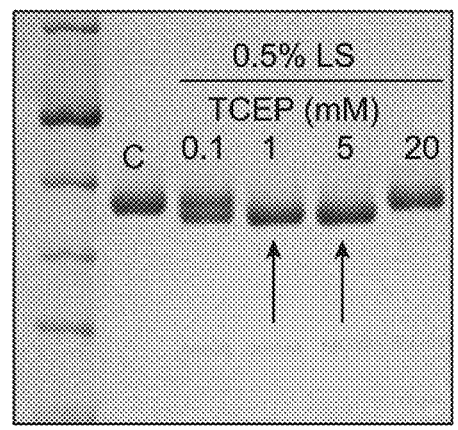
FIG. 6 shows that DTT can be substituted for tris(2-carboxyethyl)phosphine (TCEP) to enhance deglycosylation of antibody under similar conditions to those described in FIG. 5 (see also Example 6).

An anti-MBP mouse monoclonal IgG (36 µg) was mixed with varying amounts of TCEP (final concentration ranging from 0 to 20 mM) and LS (final concentration 0.5% w/v) in a total volume of 20 μL. Control reactions did not contain any deglycosylating enzyme. 1 μl Rapid PNGase F was added to all other samples and incubated for 5 minutes at 50° C. An aliquot of each sample was separated via SDS-PAGE and visualized with SimplyBlue SafeStain. Results are shown in FIG. 6.

Figure 7A:
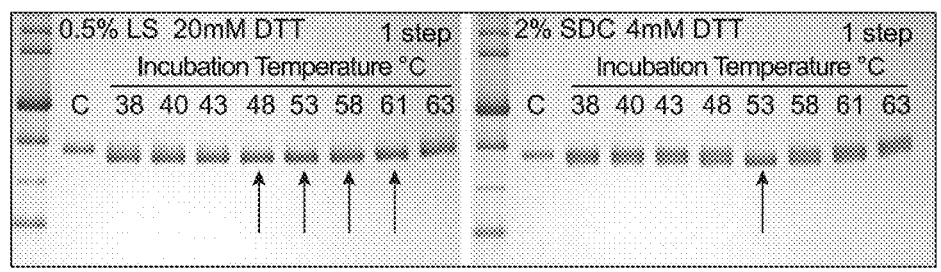
FIGS. 7A and 7B show that a range of temperatures can be used for complete deglycosylation of a mouse monoclonal IgG antibody by PNGaseF using a buffer containing a bile salt or carboxylated surfactant in combination with a reducing agent (0.5% LS and 20 mM DTT or 2% deoxycholate (SDC) 4 mM DTT) detected by a SDS-PAGE mobility shift (see arrows). Additional details for the one-step and two-step reactions are provided in Example 7.
Figure 7B:
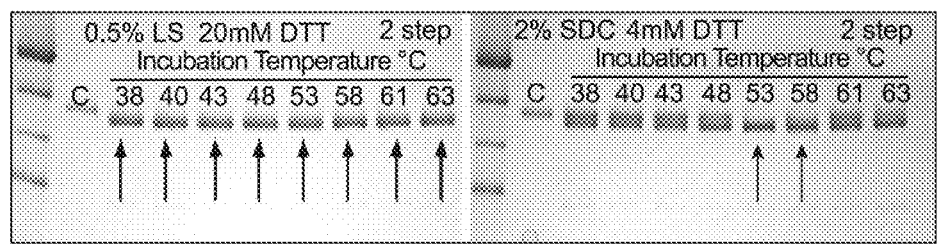

Example 7: Complete Deglycosylation of an Antibody Using a Range of Temperatures Sixteen samples of anti-MBP mouse monoclonal IgG (36 μg) were mixed with DTT (final concentration 20 mM) and LS (final concentration 0.5% w/v) in a total volume of 20 μL. Additionally, a second set of 16 samples of anti-MBP mouse monoclonal IgG (36 μg) were mixed with DTT (final concentration 4 mM) and SDC (final concentration 2% w/v) in buffer to form a total of volume of 20 μl. Eight LS-containing samples and 8 SDC-containing samples were treated in a two-step reaction by pre-incubating the sample at 50° C. for 5 minutes prior to addition of 1 μl Rapid PNGase F. 1 μl Rapid PNGase F was added to the remaining 8 LS-containing samples and 8 SDC-containing samples in a one-step reaction with no pre-incubation. Controls (separate IgG samples in the corresponding LS or SDC buffer) did not contain any PNGase F. All samples (pretreated at 50° C.; or not) were incubated for 5 minutes in a thermocycler programmed with an 8-point temperature gradient (from 38° C. to 63° C.). An aliquot of each sample was separated via SDS-PAGE and visualized with SimplyBlue SafeStain. Results are shown in FIGS. 7A-7B.

Example 8: Complete Deglycosylation of an Antibody at Ambient Temperature

An antibody can be completely deglycosylated at ambient temperature in about 5, 10 and 15 minutes using free Rapid PNGase F or immobilized forms of recombinant PNGase F. Immobilization utilized a fusion protein of PNGase F in which PNGaseF was fused via SNAP-Tag® (New England Biolabs, Ipswich, Mass.) which in turn was covalently bound to benzylguanine agarose beads. Although agarose beads were used here any suitable matrix can be used as is known in the art.

Samples of anti-MBP mouse monoclonal IgG (100 μg) were mixed with 0.5% LS and 20 mM DTT, and incubated at 37° C. for 15 minutes. Samples were loaded to a column containing PNGase F HS-BG Agarose Beads. Reactions were incubated at about 22° C. for 5, 10 or 15 minutes. A control reaction using soluble (free) PNGase F was performed under the same conditions. Negative controls ("Anti-MBP –") were not treated with enzyme.

Immobilized PNGase F or soluble Rapid PNGase F treatment resulted in a mobility shift on SDS-PAGE, corresponding to complete deglycosylation of the heavy chain of IgG. The intact mass of the control and deglycosylated antibody samples were analyzed by ESI-TOF as described in Example 1. Results are shown in FIG. 8.

Figure 9:
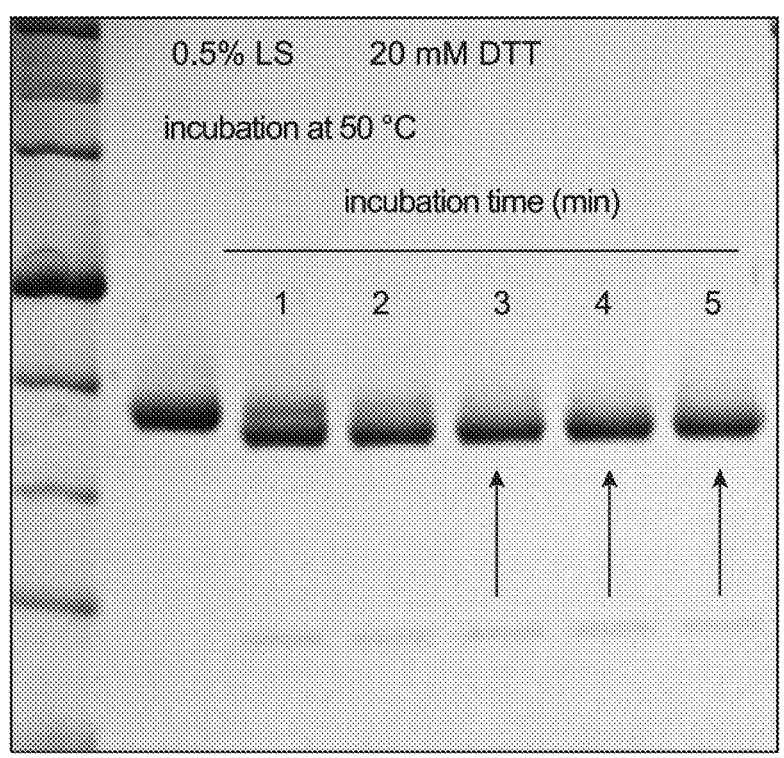
FIG. 9 shows that complete deglycosylation of an antibody using a one-step reaction (also described in Example 9) can be achieved within 3 minutes. A mouse monoclonal IgG antibody was treated with PNGase F in the presence of buffer containing a carboxylated surfactant and reducing agent for 1 to 5 minutes at 50° C. Arrows show samples where complete mobility shift is observed, indicating complete deglycosylation.

Example 9: Deglycosylation of an Antibody in 3 Minutes or Less to Produce a Substantially Deglycosylated Antibody An anti-MBP mouse monoclonal IgG (36 μg) was mixed with DTT (final concentration 20 mM) and LS (final concentration 0.5% w/v) in a total volume of 20 μL with buffer. Control reactions did not contain any PNGase F. To all other samples, 1 μl of Rapid PNGase F was added. Samples were incubated for 1 to 5 minutes at 50° C. An aliquot of each sample was separated via SDS-PAGE and visualized with SimplyBlue SafeStain (Life Technologies). The results are shown in FIG. 9. Complete deglycosylation was observed within an incubation time of three minutes.

Figure 10A:
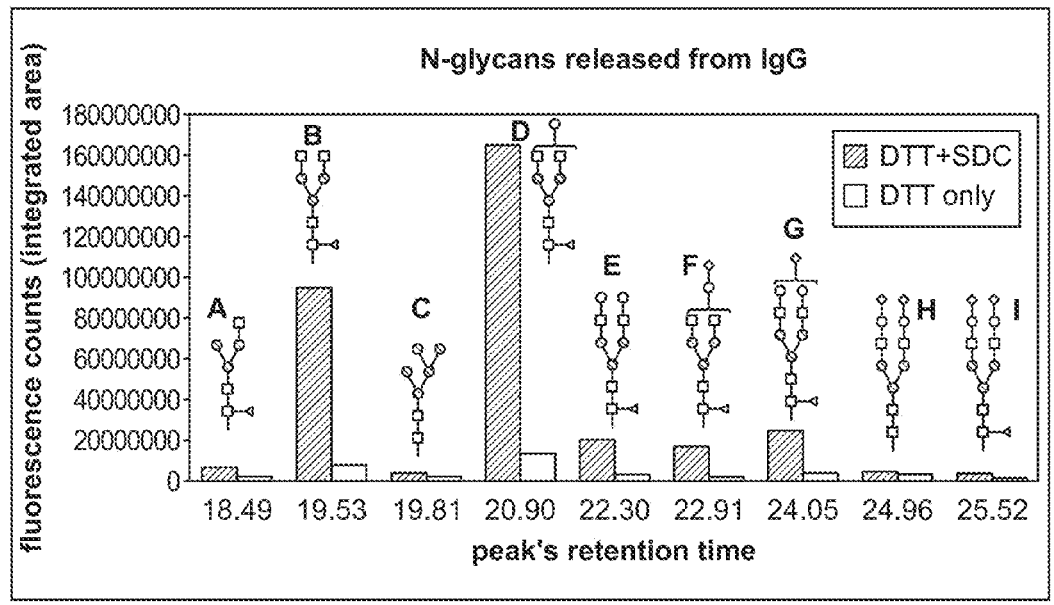
FIGS. 10A-10B graphically represents composition and characterization of N-glycans released from an antibody (see also Example 10).
Figure 10B:
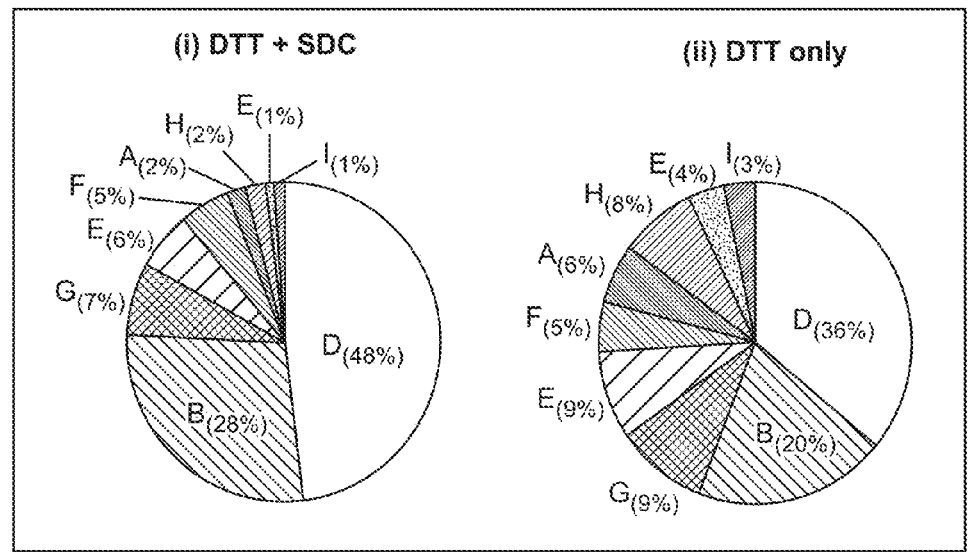

Example 10: Cleaving Substantially all N-Linked Glycans from an Antibody to Produce an Unbiased N-Glycan Composition A concentrated IgG sample was prepared as described in Example 1. Monoclonal IgG was mixed with 4 mM DTT, in the presence or absence of 2% SDC, in a total volume of 20 μL. Samples were heated to 55° C. for 10 minutes in a pretreatment followed by 1 μl Rapid PNGase (not in controls) and a second incubation of 4 hours at 37° C. The released sugars were isolated by solid phase extraction (SPE) with a graphite cartridge, dried, and labeled with 2-aminobenzamide (2AB). Samples were analyzed by LC/ESI-MS, glycan abundance was estimated by peak integration in the fluorescent channel. Glycan structures were manually assigned based on their retention time (fluorescent trace) and their corresponding m/z value. The results are shown in FIGS. 10A-10B.

Example 11: Direct Fluorescent Labeling of Glycans Released from an Antibody without Prior Glycan Purification in the Presence of a Bile Salt Aliquots (14 μg) of Anti-MBP Monoclonal Antibody were suspended in 2% SDC, and 4 mM DTT in a total volume of 20 μL. 1 μl Rapid PNGase F was added to each deglycosylation sample. Reactions were incubated for 15 minutes at 50° C. after which liberated glycans were directly labeled with 2-aminobenzamide (2AB) in the same reaction vessel (one pot), or were purified by SPE and dried as described in example 12 (two pot). Fresh labeling solution (20 μL, containing 2AB, sodium cyanoborohydride and acetic acid) was added to the dried glycans, or directly to a deglycosylation reaction (high aqueous labeling conditions). High aqueous conditions refers to a reaction having at least or about 60%, 65%, 70%, 75%, 80% or 85% (vol/vol) water. The labeling reaction was incubated at 65° C. for 2 hours after which, N-glycans were processed to removed unbound label by HILIC SPE and analyzed by LC-MS, results are shown in FIGS. 11A-11B. Similar results were obtained using a dialyzable non-cleavable carboxylated anionic surfactant in place of the bile salt (see Example 12).

Figure 12A:
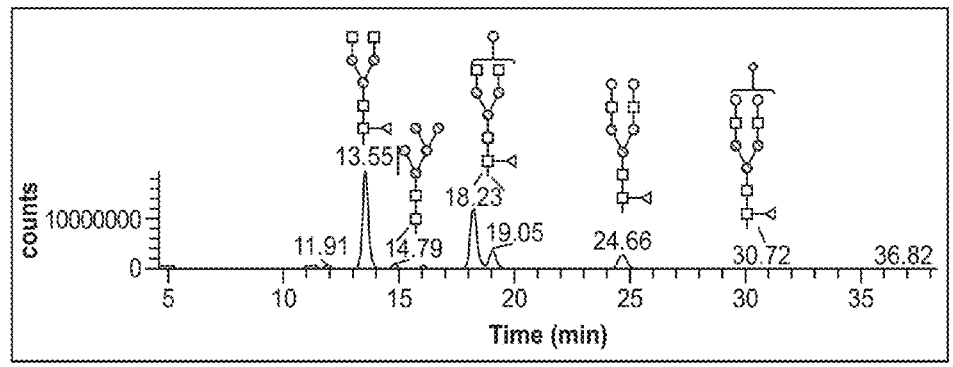
FIGS. 12A-12C show the chromatographic profiles of fluorescently labeled N-glycans released from three different antibodies in 5 minutes and labeled in a one pot method. The N-glycans were cleaved from each antibody using PNGase F in the presence of LS and DTT before labeling (see also Example 14).
Figure 12B:
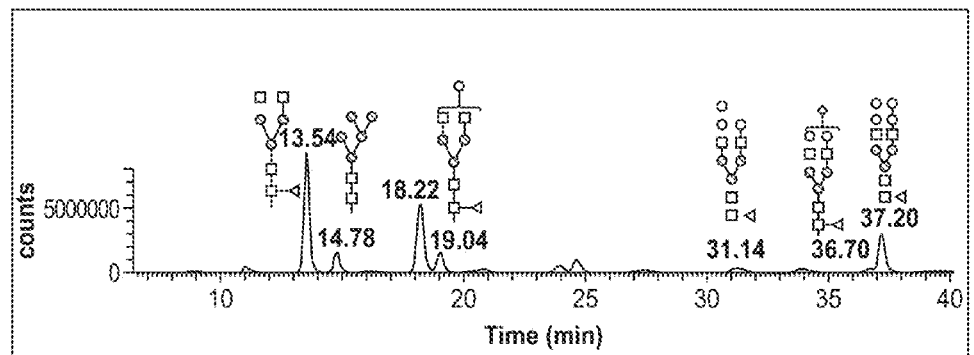
Figure 12C:
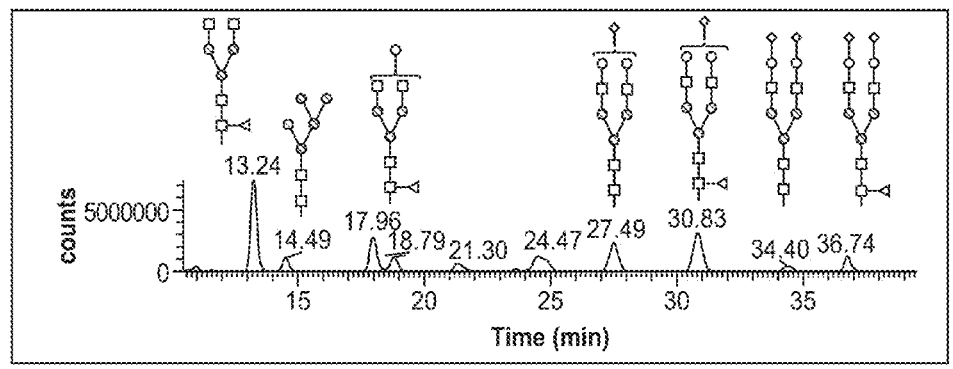

Example 12: Direct Fluorescent Labeling of Glycans Released from an Antibody without Prior Glycan Purification in the Presence of a Carboxylated Anionic Surfactant Therapeutic monoclonal IgGs and IgG fusion proteins (rituximab, cetuximab, etanercept) were deglycosylated with 20 mM DTT, 0.5% LS and Rapid PNGaseF for about 5 minutes as described in example 9, for complete deglycosylation. Immediately after, a labeling mixture (containing the reagents for reductive amination) was added and incubated for an additional 2 hours at 65° C. The labeling reaction may be performed under high aqueous conditions (described above). High aqueous conditions include >60% preferably at least or about 80% water. Fluorescently labeled glycans were subjected to HILIC SPE purification, and analyzed by HPLC-MS. Results are shown in FIGS. 12A-12C.

Example 13: Monoclonal Antibody Activity is Retained after Deglycosylation in the Presence of Iauroylsarcosine Under Reducing Conditions A concentrated IgG sample as described in Example 1 was used. The monoclonal IgG (36 µg) was mixed with 4 mM DTT and 0.5% LS in a total volume of 20 µL. Control reactions did not contain any deglycosylating enzyme. 1 µl Rapid PNGase F was added experimental samples and were incubated for 5 minutes at 50° C. The intact mass of the IgG sample was analyzed by ESI-TOF.

Figure 13A:
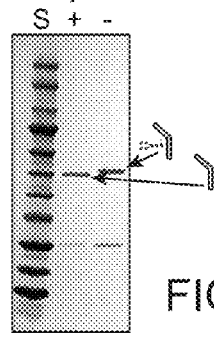
FIGS. 13A-13C demonstrate that antibodies deglycosylated by PNGase F using a combination of DTT, bile salt and mild heat are functional and retain the ability to specifically recognize and bind to its cognate antigen.
Figure 13B:
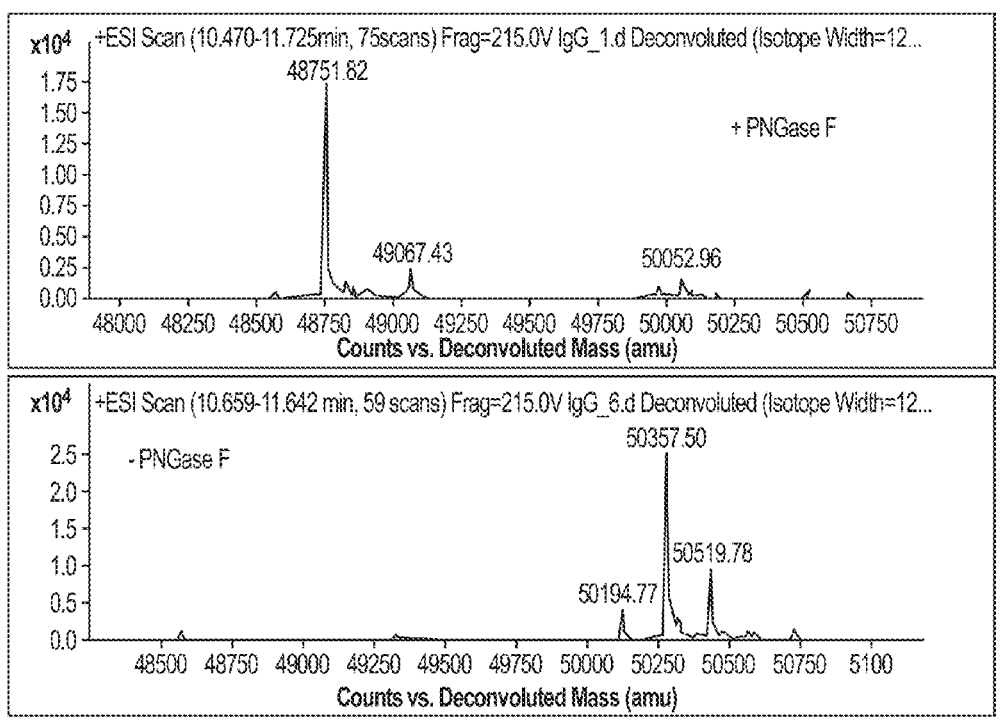
Figure 13C:
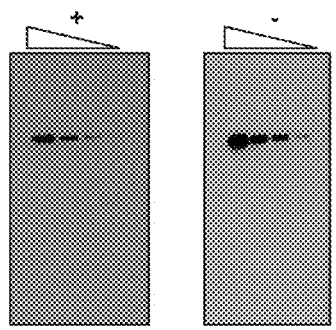

To determine the functional activity of the intact, deglycosylated monoclonal IgG, the anti-MBP-monoclonal antibody was analyzed on a Western blot against its corresponding antigen (maltose binding protein, MBP), using MBP-Endo H fusion protein (Endo Hf, New England Biolabs, Ipswich, Mass.). Western blots of serial dilutions of Endo Hf were prepared on PVDF membrane (Immobilon-P Millipore, Billerica, Mass.) and immunoblotted with either deglycosylated anti-MBP mouse monoclonal antibody (treated with PNGase F under non-reducing conditions described above) or glycosylated anti-MBP mouse monoclonal antibody (not treated with Rapid PNGase F). Results are shown in FIGS. 13A-13B.

Figure 14A:
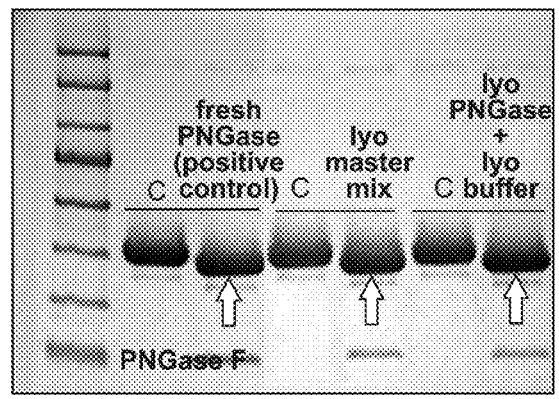
FIGS. 14A-14B demonstrate that rapid deglycosylation is effective using lyophilized PNGase F (lyo PNGase) and buffer containing a bile salt or surfactant and DTT. PNGase F and the buffer can be lyophilized either together (lyo master mix) or separately (lyo buffer) without any detrimental effect in activity (see also Example 14).
Figure 14B:
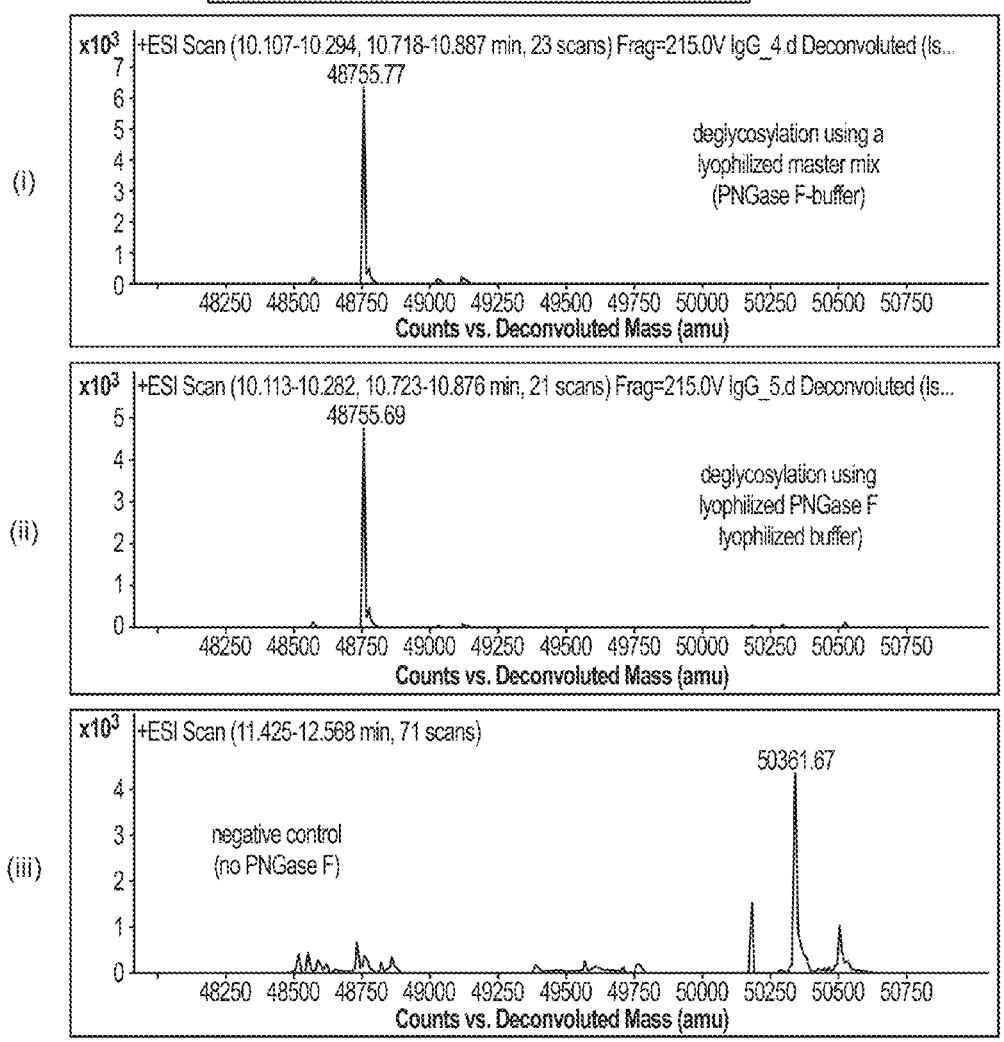
Figure 15A:
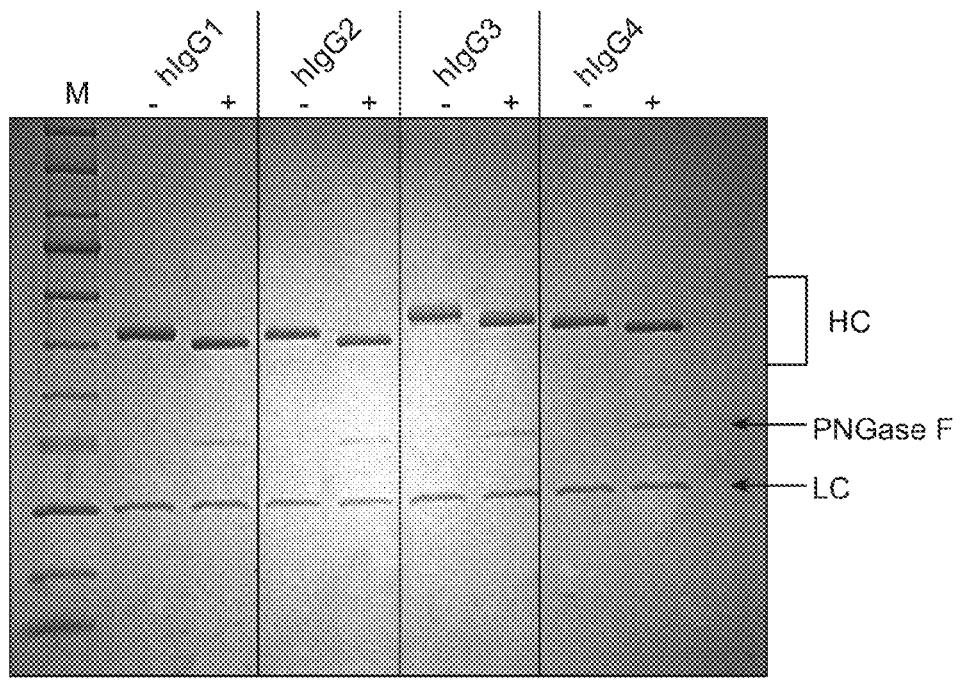
FIGS. 15A-15B illustrate that a buffer containing a bile salt or carboxylated anionic detergent and DTT can be used to efficiently deglycosylate a variety of antibody isotypes (see also Example 15). The SDS-PAGE gels show the controls (no enzyme (−)) containing buffer and the isotype antibody, but no PNGase F. (+) refers to the deglycosylation reaction using PNGase F in the presence of 0.5% LS and 20 mM DTT. The isotype and source (human, "h"; mouse "m") of the antibody are indicated. The PNGase F band is indicated on the side of each gel as well as the light chain (LC) of the isotype. Each experimental reaction showed a mobility shift of the heavy chain (the location of which is indicated by a "HC" on the side) compared with the negative control indicating successful deglycosylation.
Figure 15B:
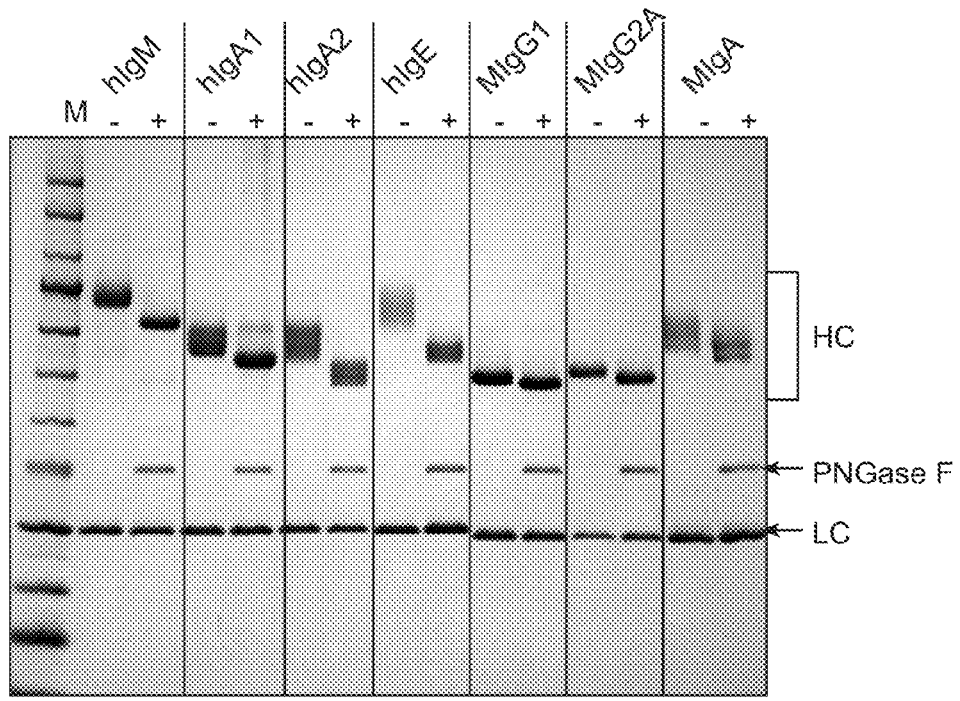

Example 14: Buffer and PNGase F can be Lyophilized Separately or in Combination and Used to Produce a Deglycosylated Antibody Rapid PNGase F and a reaction buffer containing 0.5% LS and 20 mM DTT were lyophilized either together ("master mix") or separately. Prior to testing the activity of the lyophilized master mix, or the individually lyophilized buffer and Rapid PNGase F, each component was rehydrated. Each enzyme-buffer mixture was added to an IgG sample. A negative control reaction contained 36 µg of antibody in 50 µL of fresh 0.5% LS and 20 mM DTT. A positive control reaction was identical to the negative control but with 2 µl of Rapid PNGase F. All reactions were incubated at 50° C. for 5 minutes. An aliquot of each sample was separated via SDS-PAGE and visualized with SimplyBlue SafeStain. Similar results can be achieved by substituting LS with a bile salt such as SDC (e.g. 2% SDC and 8 mM DTT) in a dried master mix or dried reaction buffer containing a bile salt as described in Examples 4 and 5. Results are shown in FIGS. 14A-14B.

Example 15: One-Step or Two-Step Complete Deglycosylation is Non-Specific for Antibody Isotypes The general effect of complete deglycosylation was demonstrated using 11 different isotypes of an antibody. The Anti-hCD20 isotype collection featuring the variable region of the therapeutic antibody rituximab was obtained from Invitrogen (San Diego, Calif.). Purified isotypes consisting of human IgG1, human IgG2, human IgG3, human IgG4, human IgM, human IgA1, human IgA2, human IgE, murine IgG1, murine IgG2a and murine IgA were used prepared at a final concentration of 1 mg/ml. Two deglycosylation reactions were set up for each isotype. A negative control reaction consisted of 16 µg of the antibody mixed with a buffer giving a final concentration of 0.5% LS, and 20 mM DTT in a total of 20 µL. Reactions were identical to the negative control, but with the addition of 1 µl Rapid PNGase F. All reactions were incubated at 50° C. for 10 minutes. An aliquot of each sample was separated via SDS-PAGE and visualized with SimplyBlue SafeStain (See FIGS. 15A-15B). Similar results have been obtained with a buffer comprising 2% SDC in place of LS.

A two-step complete deglycosylation reaction that is isotype non-specific occurs. The two-step reaction includes a brief heat pretreatment step before enzymatically cleaving the glycans. The temperature and time of the heat pre-treatment can be varied, and generally shorter times may be combined with higher temperatures. Here, the pre-treatment time is as short as one or two minutes, and the temperature can be up to about 95° C. In this example, anti-hCD20 isotype collection antibodies in a buffer containing a bile salt or a carboxylated anionic surfactant was pre-treated at 80° C. for approximately 2 minutes before adding Rapid PNGase F and incubating the mixture at 50° C. for about 10 minutes. Complete deglycosylation was confirmed by SDS-PAGE or other art-standard techniques.

Example 16: Ambient Temperature in-Line Analysis During Antibody Production

Large scale production of antibodies, such as those used for commercial or therapeutic antibody production, need analytical processes that are suitable for in-line analysis. During the production, the antibodies may need to be analyzed at multiple time points during cell cultivation to monitor the glycan profile of the glycosylated antibodies. In this example, a sample of the antibody culture was aseptically withdrawn from the bioreactor at one or more time points and loaded onto a device comprising immobilized PNGase F. The device was a column packed with beads having immobilized PNGase F. Alternatively a microfluidic device might be used with PNGase F immobilized on a surface that comes into contact with the sample. The device can be either pre-loaded or subsequently loaded with a buffer as described herein. 0.5% LS, 20 mM DTT, or 2% SDC, 20 mM DTT was used in a buffer. The sample in the device was allowed to react at ambient temperature for 15 minutes or less (e.g., 10 minutes, 5 minutes, or less) before eluting and analyzing the eluent for aglycosylation of the antibody and/or glycan composition. FIG. 8 demonstrated that immobilized PNGaseF was as effective as soluble PNGaseF in the same buffer.

Figure 16A:
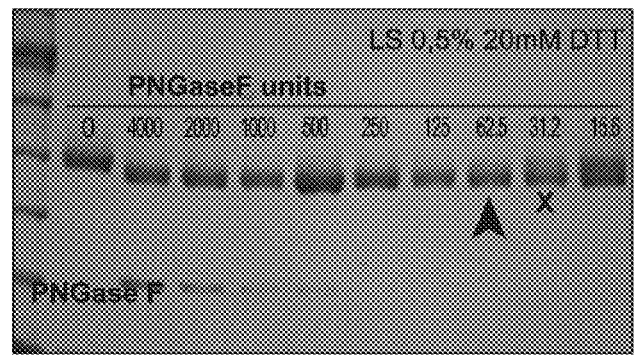
FIGS. 16A-16B shows SDS-PAGE gels in which the amount of PNGaseF required for complete deglycosylation is substantially reduced in the presence of LS and a reducing agent compared to the reducing agent alone under the otherwise same one-step reaction conditions (for experimental conditions see Example 17). The ratio of amounts (µg/µl) of PNGaseF:IgG was shown to be greater than 20 fold, greater than 50 fold, greater than 75 fold, greater than 90 fold more PNGase F in the absence of LS thus showing that complete deglycosylation can be achieved with significantly lower amounts of PNGase F in the presence of LS then would be the case without LS.
Figure 16B:
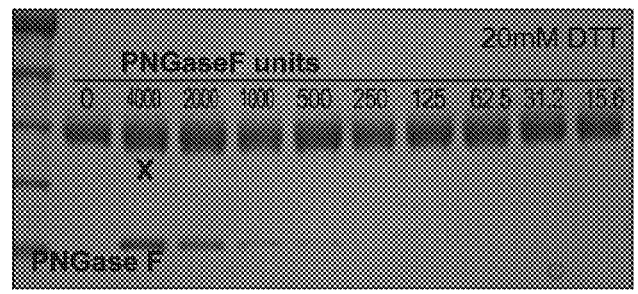

Example 17: PNGase F/IgG Ratios for Complete Deglycosylation with Reducing Agents, in Five Minutes at 50° C. (See FIGS. 16A-16B)

To determine an effective ratio of PNGaseF to antibody using a one-step reaction for five minutes at 50° C., samples of anti-MBP mouse monoclonal IgG (36 µg) were combined with DTT (20 mM), with or without LS (final concentration 0.5% w/v) in 10 µl of buffer. Controls did not contain any deglycosylating enzyme. Two-fold dilutions of stock recombinant PNGase F (8000 units/µl) were added to samples which were incubated for 5 minutes at 50° C. (one-step, simultaneous mild heating and deglycosylation). Aliquots from each tube were mixed with sample buffer, heated, and loaded on a Novex® 10-20% Tris Glycine gel (Life Technologies, Carlsbad, Calif.). After electrophoresis, the gel was stained with SimplyBlue SafeStain to visualize bands (see FIGS. 16A-16B).

Ratios for complete deglycosylation were defined as the minimal amount of units of PNGase F necessary to completely deglycosylate 1 µg of IgG in 10 µl of reaction volume at 50° C. for 5 minutes.

Figure 17A:
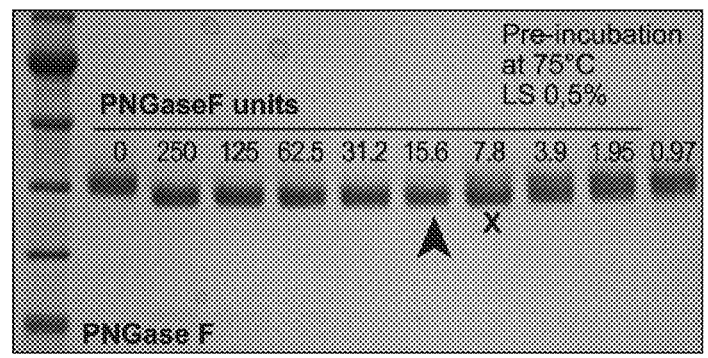
FIG. 17A-17B shows SDS-PAGE gels in which the amount of PNGaseF required for complete deglycosylation is substantially reduced in the presence of LS compared to the buffer alone under the otherwise same two-step reaction conditions. (For experimental conditions see Example 18). The ratio of PNGaseF:IgG was shown to be greater than 20 fold, greater than 50 fold, greater than 75 fold, greater than 90 fold more PNGase F in the absence of LS.
Figure 17B:
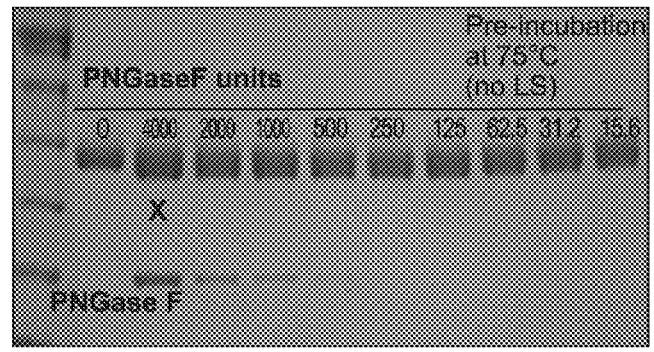

Example 18: PNGase F/IgG Ratios for Complete Deglycosylation without Reducing Agents, in a Two-Step Reaction A two-step reaction was utilized to determine an effective ratio of PNGaseF to antibody in the absence of reducing agent. Samples of anti-MBP mouse monoclonal IgG were combined with or without LS (final concentration 0.5% w/v) in 10 µl of buffer. Samples were incubated at 75° C. for five minutes. Controls did not contain any deglycosylating enzyme. Two-fold dilutions of stock recombinant PNGase F (8000 units/µl) were added to samples which were incubated for 5 minutes at 50° C. Aliquots from each tube were mixed with sample buffer, heated, and loaded on a Novex 10-20% Tris Glycine gel. After electrophoresis, the gel was stained with SimplyBlue SafeStain to visualize bands (see FIGS. 17A-17B).

Ratios for complete deglycosylation under non-reducing conditions were defined as the minimal amount of units of PNGase F necessary to completely deglycosylate 1 µg of IgG in 10 µl of reaction volume at 50° C. for 5 minutes. The results in FIGS. 16A-16B and FIGS. 17A-17B show that the presence of a dialyzable, non-cleavable carboxylation anionic surfactant significantly reduced the amount of PNGase F required for complete deglycosylation in a two-step reaction by >20 fold, >50 fold, >75 fold or >90 fold PNGase F.

Example 19: Complete Deglycosylation Under Non-Reducing Conditions Preserves Antibody Binding Function Retaining functional structure of a tetrameric antibody after deglycosylation was established as follows. Anti-MBP mouse monoclonal IgG (36 µg), rituximab (40 µg, Genentech, San Francisco, Calif.), and etanercept (25 µg, Amgen, Thousand Oaks, Calif.) were mixed with LS (final concentration 0.5% w/v) in 20 µl (final volume) of buffer. Reactions were pre-incubated under various conditions: 80° C. for 2 minutes, 75° C. for 5 minutes, 70° C. for 10 minutes, 65° C. for 10 minutes, 60° C. for 10 minutes, or 55° C. for 15 minutes. Controls did not contain any deglycosylating enzyme, to all other samples, 1 µl of Rapid PNGase F were added. Reactions were immediately incubated for 10 minutes at 50° C. Aliquots were mixed with sample buffer, heated, and loaded on a Novex 10-20% Tris Glycine gel. Non-reducing gels were also run to demonstrate structural integrity of dimers and tetramers: aliquots were mixed with sample buffer in the absence of DTT, heated, and gels were run as described above. After electrophoresis, gels were stained with SimplyBlue SafeStain to visualize bands.

Figure 18A:
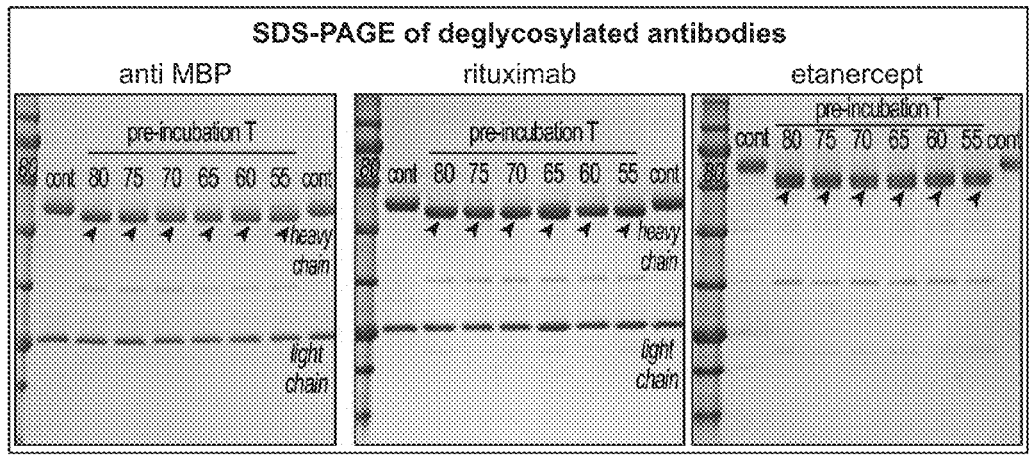
FIGS. 18A-18C shows that the conditions for PNGase F deglycosylation (carboxylic detergent, heat) under non-reducing conditions preserve the functional integrity of the antibody molecule. Mouse monoclonal IgG, rituximab, and etanercept were pre-treated under various conditions in the absence of DTT, to determine the amount of LS and the temperature and incubation time needed to promote effective deglycosylation. The deglycosylated, intact, monoclonal antibody retains its antigen binding properties (see also Example 19).
Figure 18B:
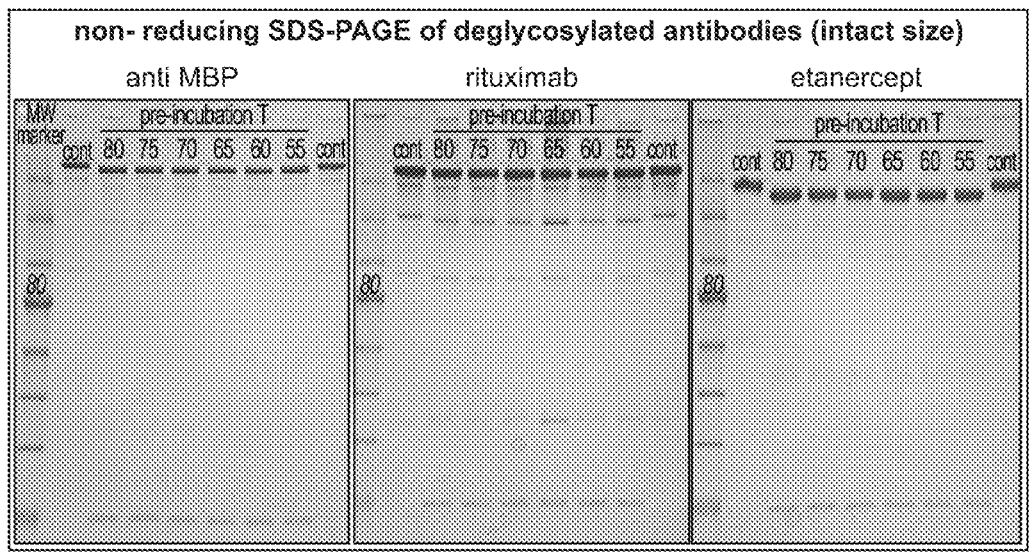
Figure 18C:
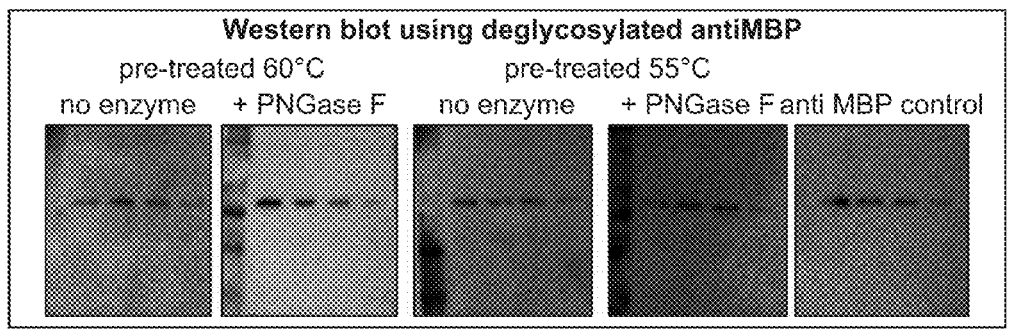

To determine the functional binding activity of the intact, deglycosylated monoclonal IgG, the anti-MBP-monoclonal antibody was analyzed on a Western blot against its corresponding antigen (maltose binding protein, MBP), using MBP-Endo H fusion protein, Endo Hf. Western blots of serial dilutions of Endo Hf were prepared on PVDF membrane (Immobilon-P Millipore) and immunoblotted with either deglycosylated anti-MBP Mouse monoclonal antibody (treated with PNGase F under non-reducing conditions described above) or glycosylated anti-MBP mouse monoclonal antibody (not treated with PNGase F). Controls with fresh anti-MBP were also included. Results are shown in FIGS. 18A-18C.

Figure 19:
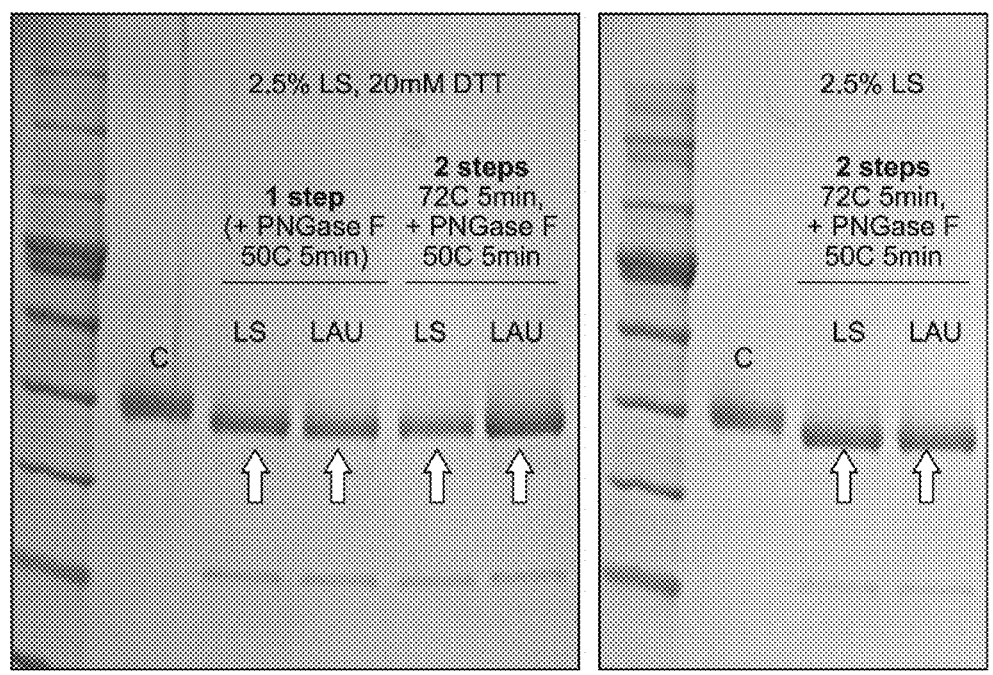
FIG. 19 shows that rapid deglycosylation is effective using carboxylic surfactants such as LS or sodium laurate (LAU) (see example 20). The SDS-PAGE shift in migration indicates complete deglycosylation (arrows) can be compared with the control ("C"). The carboxylic acid is effective in the presence or absence of a reducing agent. The figure also shows that a carboxylic acid is effective for rapid deglycosylation in 5 minutes at 50° C. in a one-step or two-step reaction.

Example 20: Complete Deglycosylation of Antibody in a One-Step or Two-Step Reaction with PNGase F Treatment in the Presence of Two Different Dialyzable, Non-Cleavable Carboxylated Surfactants Aliquots (36 µg) of anti-MBP monoclonal antibody were suspended in a buffer containing either 2.5% LS or laurate (LAU), with or without 20 mM DTT, in a 20 µL volume of buffer. Control reactions did not contain PNGase F. For the one-step reactions, 1 µL of Rapid PNGase F was added and samples were incubated at 50° C. for 5 minutes. For the two-step reactions, samples were pre-heated at 72° C. for 5 minutes, after cooling 1 µL of Rapid PNGase F was added and samples were incubated at 50° C. for 5 minutes. Aliquots (5.4 µg IgG) of each sample were separated via SDS-PAGE and visualized with SimplyBlue SafeStain (see FIG. 19)

Example 21: Simultaneous Digestion of a Protein with PNGase F and Trypsin

Simultaneous PNGase F/Trypsin digestion was performed to facilitate peptide mapping (and peptide coverage) of monoclonal antibodies. This single-step method is advantageous for structural analysis, such as glycan occupancy determination and compares favorably with recombinant PNGase F digestion followed by Trypsin digestion that requires several hours to complete.

To determine the deglycosylation conditions that were favorable for protease digestion, 25 µg of anti-MBP mouse monoclonal IgG were resuspended in a total of 50 µl of buffer. The antibody was incubated at 95° C. for 5 minutes, and then 6 µl of Rapid PNGase F and 250 µg of Trypsin-ultra™, Mass Spectrometry Grade (New England Biolabs, Ipswich, Mass.) at a ratio 1:100 enzyme:substrate. The samples were incubated at 37° C. for 30 minutes to 3 hours, or 50° C. for 5 minutes to 30 minutes.

Figure 20A:
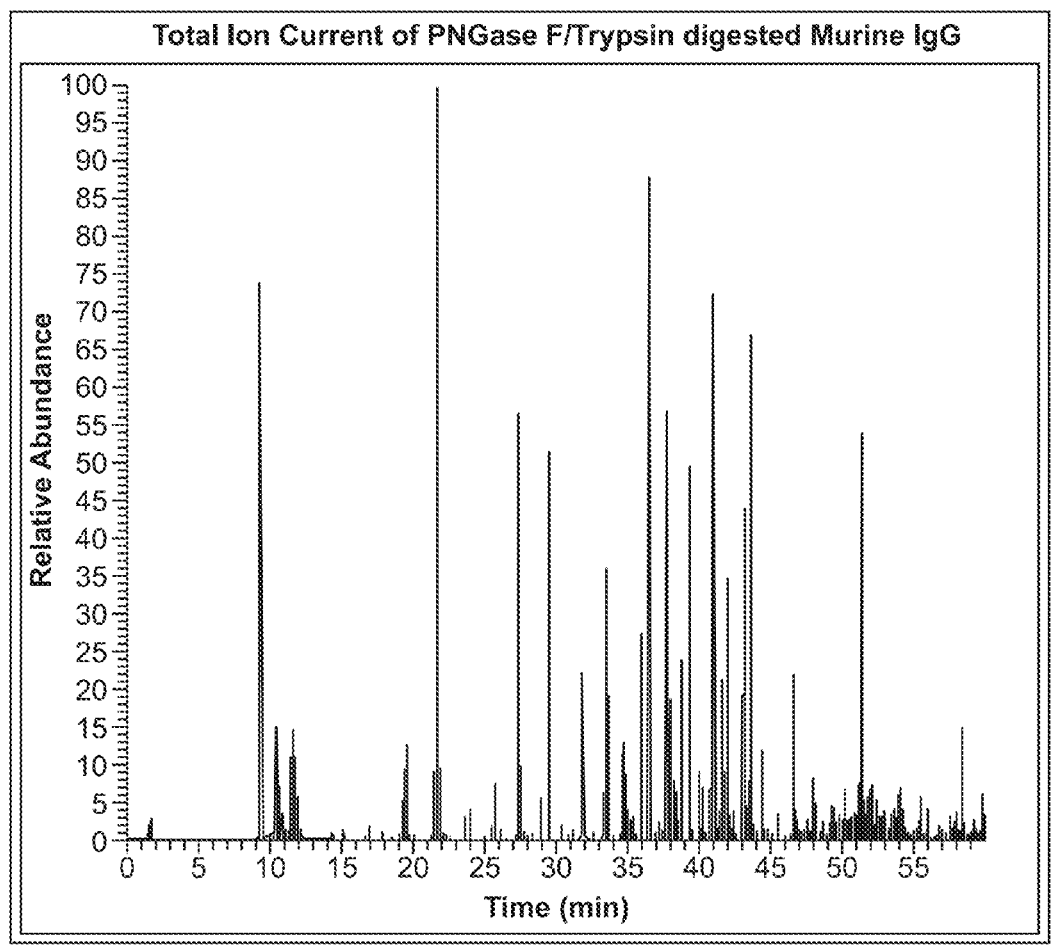
FIGS. 20A-20B shows the results of simultaneous Rapid PNGase F (New England Biolabs, Ipswich, Mass.) and Trypsin reactions. Rapid deglycosylation occurs in the presence of a proteolytic enzyme such as Trypsin (see example 21). Mouse monoclonal IgG was simultaneously deglycosylated with PNGase F and cleaved by trypsin to yield deglycosylated, tryptic peptides for mass spectrometry analysis.
Figure 20B:
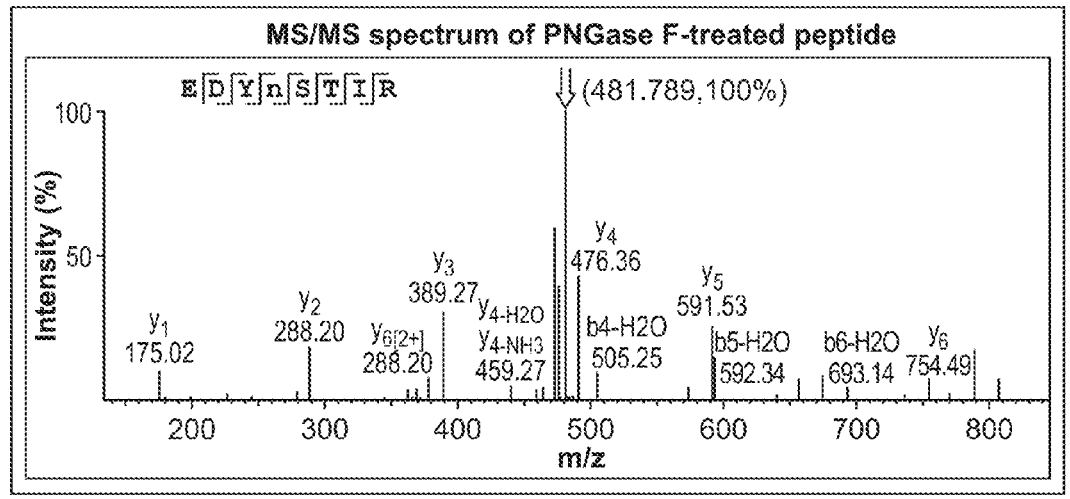

One microliter of digested sample (simultaneous PNGase F/trypsin digestion) was injected onto a C18 analytical column and separated using a 60 minute linear gradient. Multiple-charged peptide ions were automatically chosen and fragmented by both CID and ETD. The MS and MS/MS fragmentation data were analyzed, considering theoretical peptides with a maximum of two missed cleavages. The analysis allowed variable modifications of asparagine to account for the conversion to aspartic acid that occurs after the glycan removal by PNGase F. While the data in FIGS. 20A-20B shows results for PNGase F/Trypsin in the absence of LS, the present example provides a method for doing the reaction in the presence of a carboxylated anionic surfactant.

Example 22: Complete Deglycosylation of an Antibody Containing Both N- and O-Glycans in a Two-Step Reaction, Involving Pre-Treatment with Heat in Combination with a Bile Salt or Non-Cleavable Dialyzable Carboxylated Surfactant Prior to Treatment with a Combination of Glycosidases For antibodies containing O-glycans, it may be desirable to optionally remove all O-glycans as well as N-glycans.

Enzyme combinations containing an O-glycosidase (Endo-alpha-N-acetylgalactosaminidase) and 3 exoglycosidases (neuraminidase, Beta 1-4 galactosidase and Beta N-Acetyl glucosaminadase (New England Biolabs, Ipswich, Mass.)) for cleaving O-glycans and N-glycosidases (PNGase F) for cleaving N-glycans were used together to completely deglycosylate a protein having O- and N-glycans.

A therapeutic monoclonal fusion protein (etanercept) was mixed with 0.5% LS and 20 mM DTT. Samples were pre-incubated at 80° C. for 2 minutes. 5 μl of Protein Deglycosylation Mix containing all the glycosidases described above (New England Biolabs, Ipswich, Mass.) were added to samples. Control reactions included no enzyme; or SDS in place of LS, reactions were incubated for 30 minutes at 37° C. An aliquot of each sample was separated via SDS-PAGE and visualized with SimplyBlue SafeStain.

Samples treated with Protein Deglycosylation Mix show an increase in mobility compared with controls corresponding to complete removal of both O-glycans and N-glycans. This example underscores problems with the use of SDS which is detrimental to complete deglycosylation by the enzyme mix.

For all patents, applications, or other references cited herein, such as non-patent literature and reference sequence information (such as database or accession numbers) are incorporated by reference in its entirety for all purposes as well as for the proposition that is recited. Where any conflict exits between a document incorporated by reference and the present application, this application will control.

As will be recognized by the person having ordinary skill in the art following the teachings of the specification, the foregoing aspects can be claimed by Applicant in any combination or permutation. To the extent one or more elements and/or features is later discovered to be described in one or more references known to the person having ordinary skill in the art, they may be excluded from the claims by, inter alia, a negative proviso or disclaimer of the one or more elements and/or features. Headings used in this application are for convenience only and do not affect the interpretation of this application or claims.

What is claimed is:

1. A composition, comprising:
   (i) a bile salt or a dialyzable non-cleavable carboxylated anionic surfactant;
   (ii) peptide-N-glycosidase F (PNGase F);
   (iii) a deglycosylated antibody wherein the deglycosylated antibody is an N-glycosylated antibody from which at least 90% of the N-glycans have been removed; and
   (iv) glycan cleavage products;
   wherein the composition does not comprise sodium dodecyl sulfate (SDS).

2. The composition according to claim 1, wherein the composition comprises a bile salt.

3. The composition according to claim 1, wherein the deglycosylated antibody has antigen binding activity.

4. The composition according to claim 3, wherein the deglycosylated antibody is selected from deglycosylated human IgG1, human IgG2, human IgG3, human IgG4, human IgM, human IgA1, human IgA2, human IgE, murine IgG1, murine IgG2a and murine IgA.

5. The composition according to claim 3, wherein the deglycosylated antibody is suitable for use in an immunoassay.

6. The composition according to claim 1, wherein the glycan cleavage products and/or the deglycosylated antibody are labeled with a fluorescent label, a radioisotope, methyl acetyl, an antibody or a combination thereof.

7. The composition according to claim 1, further comprising a protease.

8. The composition according to claim 7, wherein the protease is trypsin.

9. The composition according to claim 7, wherein the protease is selected from trypsin, GluC, AspN, proteinase K, Factor Xa, Enterokinase, LysC, Arg-C, LysN, IdeS, V-8 Protease, Papain, Alpha-Lytic Protease, Pyroglutamate Aminopeptidas, Leucine Aminopeptidase, Methionine Aminopeptidase, Aminopeptidase I, Aminopeptidase A, Carboxypeptidases (A, B, G, Y), pepsin, Cathepsins (B, C, D), α-Chymotrypsin, TEV, thrombin, IdeZ and IdeE.

10. The composition according to claim 1, wherein the PNGase F is a fusion protein.

11. The composition according to claim 10, wherein the fusion protein is immobilized on a matrix.

12. The composition according to claim 10, wherein the fusion protein comprises a mutant 06-alkylguanine-DNA-alkyltransferase (AGT) and optionally is immobilized through affinity binding of the AGT to a matrix.

13. The composition according to claim 1, wherein the composition further comprises a buffering agent.

14. The composition according to claim 1, wherein the composition comprises a dialyzable non-cleavable carboxylated anionic surfactant.

15. A method for removing N-glycans from an antibody, comprising incubating a composition lacking SDS comprising:
   i. a bile salt or a dialyzable non-cleavable carboxylated anionic surfactant,
   ii. peptide-N-glycosidase F (PNGase F), and
   iii. an N-glycosylated antibody,
   for less than 60 minutes, to remove at least 90% of the N-glycans from the N-glycosylated antibody to produce a deglycosylated antibody.

16. The method according to claim 15, further comprising isolating the deglycosylated antibody or cleaved glycan products.

17. The method according to claim 15, further comprising characterizing the deglycosylated antibody and/or the glycan cleavage products.

18. The method according to claim 15, further comprising determining the antigen binding activity of the deglycosylated antibody.

19. The method according to claim 18, comprising determining an activity of the deglycosylated antibody by an antibody-antigen binding assay selected from a radioimmune assay, an ELISA, an affinity binding assay, or an immunoprecipitation assay.

20. The method according to claim 15, wherein the deglycosylated antibody is a therapeutic antibody.

21. The method according to claim 15, wherein the deglycosylated antibody is a diagnostic antibody.

22. The method according to claim 15, wherein the composition further comprises a protease for forming a mixture of peptide fragments and glycan cleavage products.

23. The method according to claim 15, wherein the glycosidase is immobilized on a matrix.

24. The method according to claim 15, wherein the incubating is at a temperature in the range of about 20° C. to about 60° C.

25. The composition according to claim 1, wherein the deglycosylated antibody is an N-glycosylated antibody from which at least 98% of the N-glycans have been removed.

26. The method according to claim 15, wherein the deglycosylated antibody is an N-glycosylated antibody from which at least 98% of the N-glycans have been removed.

* * * * *